US012791516B2

(12) United States Patent
Kim et al.

(10) Patent No.: US 12,791,516 B2
(45) Date of Patent: Nov. 10, 2026

(54) BIOSENSOR CARTRIDGE AND BIOSENSOR DIAGNOSTIC DEVICE FOR READING SAME

(71) Applicant: LG ELECTRONICS INC., Seoul (KR)

(72) Inventors: Kyounghwa Kim, Seoul (KR); Taekyu Choi, Seoul (KR); Younghwan Kim, Seoul (KR); Seonggeun Kim, Seoul (KR); Kyungho Kong, Seoul (KR); Changseok Kim, Seoul (KR); Kyoungtaek Lim, Seoul (KR); Youngrae Lee, Seoul (KR); Inkwan Yeo, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 853 days.

(21) Appl. No.: 17/993,833

(22) Filed: Nov. 23, 2022

(65) Prior Publication Data

US 2023/0330662 A1 Oct. 19, 2023

(30) Foreign Application Priority Data

Apr. 19, 2022 (KR) ........................ 10-2022-0047913

(51) Int. Cl.
*G01N 27/414* (2006.01)
*A61B 5/05* (2021.01)
(Continued)

(52) U.S. Cl.
CPC ........... *G01N 27/4145* (2013.01); *A61B 5/05* (2013.01); *A61B 10/0045* (2013.01);
(Continued)

(58) Field of Classification Search
CPC ............. G01N 27/4145; G01N 27/414; G01N 33/48785; G01N 33/5438;
(Continued)

(56) References Cited

U.S. PATENT DOCUMENTS 9,805,165 B2 10/2017 Xiang et al.
11,342,051 B1 5/2022 Jain et al.
(Continued)

FOREIGN PATENT DOCUMENTS

CA 3175822 A1 10/2021
JP 2000-258493 A 9/2000
(Continued)

OTHER PUBLICATIONS

Cheah et al., "Integrated Platform Addressing the Finger-Prick Blood Processing Challenges of Point-of-Care Electrical Biomarker Testing", Analytical Chemistry, vol. 94, No. 1, published Jan. 3, 2022, pp. 1256-1263.
(Continued)

*Primary Examiner* — Samuel P Siefke
(74) *Attorney, Agent, or Firm* — Birch, Stewart, Kolasch & Birch, LLP

(57) ABSTRACT

A biosensor cartridge includes: a circuit board that is electrically connectable to an external diagnostic device; a sensor chip for detecting a target material from an applied analysis specimen, have a reactant reacting specifically with the target material, and transmitting an electrical signal generated by reacting with the detected target material to the connection terminal of the circuit board; and a housing accommodating the circuit board and the sensor chip and surround the circuit board and the sensor chip so that the connection terminal is exposed, and the housing including a QR code having stored therein encrypted sensor information. Accordingly, a separate memory chip that stores envi-
(Continued)

ronment information for genuine product certification of the biosensor on the circuit substrate is not mounted, and the cost is saved, and there is an effect of minimizing the volume of the cartridge.

10 Claims, 16 Drawing Sheets

(51) Int. Cl.
*A61B 10/00* (2006.01)
*G01N 33/487* (2006.01)
*G01N 33/543* (2006.01)

(52) U.S. Cl.
CPC ..... *G01N 27/414* (2013.01); *G01N 33/48785* (2013.01); *G01N 33/5438* (2013.01); *B01L 2200/027* (2013.01); *B01L 2300/0636* (2013.01); *B01L 2300/0645* (2013.01); *B01L 2300/0663* (2013.01); *H01R 2201/20* (2013.01); *H05K 2201/10151* (2013.01)

(58) Field of Classification Search
CPC ....... G01N 33/48707; G01N 33/48771; G01N 33/48778; G01N 33/48792; G01N 27/4146; A61B 5/05; A61B 10/0045; A61B 5/0077; A61B 5/14546; A61B 5/1468; A61B 5/1486; A61B 5/4887; A61B 5/0002; A61B 5/061; A61B 2562/08; B01L 2200/027; B01L 2300/0636; B01L 2300/0645; B01L 2300/0663; B01L 3/502715; H01R 2201/20; H01R 13/465; H01R 13/6683; H01R 2201/12; H01R 12/72; H05K 2201/10151; H05K 2201/10265; H05K 1/181; H05K 2201/10166; H05K 2201/10386; G06K 7/1417; G06K 7/1447; G06Q 20/3223
See application file for complete search history.

(56) References Cited

U.S. PATENT DOCUMENTS

| | | | |
|---|---|---|---|
| 12,455,258 | B2 | 10/2025 | Kim et al. |
| 2004/0244151 | A1 | 12/2004 | Sakata et al. |
| 2008/0280285 | A1 | 11/2008 | Chen et al. |
| 2009/0124876 | A1 | 5/2009 | Nakamura et al. |
| 2014/0052475 | A1 | 2/2014 | Madan et al. |
| 2014/0273187 | A1 | 9/2014 | Johnson et al. |
| 2014/0308459 | A1 | 10/2014 | Miyazaki et al. |
| 2015/0083589 | A1 | 3/2015 | Lee et al. |
| 2015/0268186 | A1 | 9/2015 | Pagels |
| 2015/0352550 | A1 | 12/2015 | Bhargava et al. |
| 2016/0084793 | A1 | 3/2016 | Chen et al. |
| 2018/0272342 | A1 | 9/2018 | Samsoondar |
| 2019/0041355 | A1 | 2/2019 | Merriman et al. |
| 2019/0234907 | A1 | 8/2019 | Edwards et al. |
| 2020/0108385 | A1* | 4/2020 | Temiz ............... B01L 3/502715 |
| 2020/0170552 | A1 | 6/2020 | Cho et al. |
| 2020/0333286 | A1 | 10/2020 | Leon et al. |
| 2021/0003528 | A1 | 1/2021 | Esquivel-Upshaw et al. |
| 2021/0129133 | A1 | 5/2021 | Ohta et al. |
| 2021/0285977 | A1 | 9/2021 | Tu et al. |
| 2021/0365445 | A1 | 11/2021 | Robell et al. |

FOREIGN PATENT DOCUMENTS

| | | | |
|---|---|---|---|
| JP | 2003-149192 | A | 5/2003 |
| JP | 2008-46094 | A | 2/2008 |
| JP | 2013-83506 | A | 5/2013 |
| JP | 2020-126077 | A | 8/2020 |
| KR | 20-0311804 | Y1 | 5/2003 |
| KR | 10-0813398 | B1 | 3/2008 |
| KR | 10-2008-0110356 | A | 12/2008 |
| KR | 10-2010-0072533 | A | 7/2010 |
| KR | 10-2010-0103932 | A | 9/2010 |
| KR | 10-2011-0064754 | A | 6/2011 |
| KR | 10-2012-0101806 | A | 9/2012 |
| KR | 10-2013-0012744 | A | 2/2013 |
| KR | 10-1323373 | B1 | 10/2013 |
| KR | 10-2014-0120138 | A | 10/2014 |
| KR | 10-1507317 | B1 | 3/2015 |
| KR | 10-2016-0017684 | A | 2/2016 |
| KR | 10-1591379 | B1 | 2/2016 |
| KR | 10-2016-0065562 | A | 6/2016 |
| KR | 10-1779705 | B1 | 9/2017 |
| KR | 10-2030272 | B1 | 10/2019 |
| KR | 10-2019-0136580 | A | 12/2019 |
| KR | 10-2021-0076854 | A | 6/2021 |
| KR | 10-2021-0151487 | A | 12/2021 |
| WO | WO 2019/208901 | A1 | 10/2019 |
| WO | WO 2021/013392 | A1 | 1/2021 |
| WO | WO 2021/224907 | A1 | 11/2021 |

OTHER PUBLICATIONS

Tran et al., “Toward Intraoperative Detection of Disseminated Tumor Cells in Lymph Nodes with Silicon Nanowire Field Effect Transistors”, ACS Nano, vol. 10, No. 2, published on Feb. 9, 2016, pp. 2357-2364.

Sommers et al., “Self-propelled water droplet movement on a laser-etched radial gradient copper surface,” Applied Thermal Engineering, vol. 173, No. 115226, 2020, pp. 1-12.

* cited by examiner

BIOSENSOR CARTRIDGE AND BIOSENSOR DIAGNOSTIC DEVICE FOR READING SAME

CROSS-REFERENCE TO RELATED APPLICATIONS

This application claims priority to the Korean Patent Application No. 10-2022-0047913 filed in the Republic of Korea on Apr. 19, 2022, which is hereby incorporated by reference in its entirety into the present application.

BACKGROUND

Field

This disclosure relates to a biosensor system including a biosensor cartridge having a biosensor and a diagnostic device for diagnosing disease by reading information of the biosensor cartridge.

Discussion of the Related Art

Recently, as diseases having a high infectivity spread, a need for rapid diagnosis and self-diagnosis of the disease in medical fields, such as homes, hospitals, and public health centers, is increasing.

Therefore, it is required to develop an immunoassay platform that does not require specialized knowledge or complicated procedures and has a short analysis time.

A biosensor generates an electrical, optical signal, and a color that changes according to a selective reaction between probe material having reactivity for a specific target material contained in a body fluid, such as sweat and saliva, or in biological substances such as blood or urine, and the target material. Accordingly, the presence of a specific target material can be checked by using the biosensor.

Conventionally, a strip-type rapid kit has been widely used, and simple color development (e.g., the test, such as a dipstick, will change colors if the results are positive) is performed by determining whether a bio-target material having a certain concentration or higher is present.

However, in the case of labeling the target material by color development, the conversion of color development can be inaccurate depending on the concentration of the target material, and the color development must be visually determined. Therefore, the accuracy is different depending on a user who views the test results.

To compensate for this inaccuracy, a biosensor that generates an electrical signal, as opposed to a color development, has been proposed.

In a biosensor that generates an electrical signal, a target material is coupled to a small thin film semiconductor structure, an electrical conductivity of the semiconductor structure is changed by the target material, and the target material is detected through a change in electrical conductivity. In particular, when a target material is combined in a channel, if an electrochemical reaction occurs or the target material itself has a charge, electrons or holes in the semiconductor structure are accumulated or depleted due to the electric field effect caused by the combination of the probe material and the target material. Thus, the electrical conductivity is changed, which is read as a change in the amount of current. In such an electrochemical-based biosensor, the resistance of an electrode itself and the interfacial property of a channel where the electrochemical reaction occurs can be rather important.

Meanwhile, in the biosensor having a channel of a semiconductor structure as mentioned above, an electrode for measuring an electrical signal is also manufactured in a dicing unit and the thickness thereof is very thin, and damage of the electrode or channel occurs in a coupling process with a measurement device for measuring current, and therefore, a short circuit or contamination can occur.

To prevent this possibility of a short circuit, the conventional biosensor is provided as a structure including a sensor for sensing a target material and a connector for connecting with (e.g., to) the measurement device.

That is, the electrode of the conventional biosensor is extended from the sensor for sensing a target material and includes the connector for connecting with the measurement device.

However, even in the case that the electrode is extendedly formed, since the electrode is formed in a dicing process (e.g., a process where a sheet of electrodes is diced or cut into individual electrodes, which may be performed using a laser, for instance), the size of the sensor chip becomes greater, which can cause a limitation that the semiconductor wafer becomes greater unnecessarily, and therefore, the chip yield becomes degraded.

Furthermore, when the conventional biosensor contacts the measurement device and detects a signal from the electrode, an external force is exerted directly on the biosensor chip, and a crack can occur in the sensor chip.

In addition, conventionally, a dedicated measurement device is used to measure a signal of the biosensor.

The dedicated measurement device is huge and requires a precise measurement device that is expensive, and since the measurement process is performed manually, the dedicated measurement device has poor reproducibility and long diagnosing time, and requires an equipment of high price to construct the system.

Particularly, a separate reader is required to read a barcode to receive genuine product certification or sensor information of each biosensor, and an input process is required via information transmission and reception between the reader and the measurement device or a manual input.

In addition, in the case that a concentration is periodically measured for blood sugar, glycosuria, or blood pressure, or in the case that a recurrent disease needs to be periodically observed after a treatment, a high-sensitivity measurement of a bio material minutely present in body fluid is required, and there is a problem that a system development is required whenever a new disease occurs, and therefore, a multipurpose use of the system can be difficult.

For this, a simplified measurement device has been proposed. However, a contact of a bio target material for a detection occurs in the state that the measurement device is coupled with a sensor, and contamination of the measurement device and a reliability problem occur for the accuracy when the sensor is replaced.

For such a dedicated measurement device, it is not practically easy to be equipped with the dedicated measurement device in a private hospital or a home, and for the simplified measurement device, there can be a reliability limitation, and an active application can be difficult.

SUMMARY OF THE DISCLOSURE

The disclosure has been made in view of the above limitations, and can provide a biosensor cartridge including a sensor chip, and minimize the influence exerted on the sensor chip when being connected with a diagnostic device.

The disclosure can further provide an integral diagnostic device, and provide a compact diagnostic device capable of reading detection information of the sensor chip by inserting a terminal of the biosensor cartridge.

The disclosure can further provide a biosensor cartridge accommodating a circuit substrate connected with a sensor chip, and provide a biosensor cartridge capable of saving cost by replacing a separate memory chip for storing environment information for genuine product certification of the biosensor by QR codes on an outer surface of the cartridge, not mounting the separate memory chip on the circuit substrate.

The disclosure can further provide a biosensor system in which the diagnostic device reads the environment information of the biosensor cartridge when a terminal of the biosensor cartridge is inserted to the integrated diagnostic device, and a separate operation or device for obtaining the environment information is not required.

In accordance with an aspect of the present disclosure, a biosensor cartridge includes: a circuit board including a connection terminal configured to be electrically connectable to an external diagnostic device; a sensor chip configured to detect a target material from an applied analysis specimen, have a reactant reacting specifically with the target material, and transmit an electrical signal generated by reacting with the detected target material to the connection terminal of the circuit board; and a housing configured to accommodate the circuit board and the sensor chip and surround the circuit board and the sensor chip so that the connection terminal is exposed, wherein a QR code in which sensor information is encrypted and stored is attached to a surface of the housing.

The connection terminal can be formed with being protruded from a side surface of the housing, and the QR code can be attached to a lower surface of the housing.

The sensor chip can include: a sensor area in which a channel to which a reaction material reacting with the target material is attached; and a pad area for transmitting an electronic signal delivered from the sensor area to the circuit substrate, wherein the sensor area can include: a substrate, a channel area in which at least one of the channel is formed on the substrate, a source electrode and a drain electrode overlapped with both ends of the channel and formed spaced apart from each other, a gate electrode spaced apart from the source electrode and the drain electrode and introducing bias voltage to the analysis specimen, and a passivation layer for covering the entire sensor area and opening only an upper portion of the channel area and the gate electrode.

The housing can have an inclined surface dent from an upper surface and form an accommodating portion that exposes the sensor area of the sensor chip and accommodates the test specimen.

The sensor information encrypted by the QR code can include at least one of the sensor chip type, linker information, probe material information, product ID, board ID, or manufacturer information.

The QR label on which the QR code is printed can be a VOID label.

In accordance with another aspect of the present disclosure, a diagnostic device for a biosensor cartridge that generates an electronic detection signal depending on a target material in an applied analysis specimen, the diagnostic device includes: a cover member for accommodating a main board for mounting at least one functional module in internal space; a front panel for covering an upper surface of the cover member and providing a display area and an insertion hole of the at least one biosensor cartridge; a control module mounted on the main board, for reading a presence of the target material by analyzing a detection signal from the biosensor cartridge and displaying the presence of the target material in the display area; and a QR reading module disposed on a front end of the insertion hole, for reading a QR code of the biosensor cartridge when the biosensor cartridge is inserted.

The plurality of channels can be disposed to be spaced apart at the same angle from the center of the open area.

The control module can obtain sensor information for the QR code from the QR reading module and perform genuine product certification with the server based on the sensor information.

The control module can transmit a certification request to a highest priority server among a plurality of servers, and based on a certification response being not received within a predetermined time, the control unit can transmit the certification request to the next highest priority cloud server.

The control module can transmit at least a part of the sensor information and receive the certification result on whether the biosensor cartridge is a genuine product by comparing the sensor information and the information of the biosensor cartridge.

The control module can read the detection signal from the biosensor cartridge when the biosensor cartridge inserted in the insertion hole is certified as a genuine product and read whether the target material is present.

The control module can receive read correction data for the biosensor cartridge from the server when the certification is completed and updates read algorithm by the read correction data.

An insertion detection signal can be transmitted to the control module when a connection terminal of the biosensor cartridge is inserted into the insertion hole.

The front channel can be formed at a front end of the insertion hole and include an opening exposing the QR reading module disposed at a lower side of the front panel, and wherein the control module can read the QR code of the biosensor cartridge in which the connection terminal of the QR reading module is inserted into the insertion hole.

The QR reading module can include a QR reader device for photographing the QR code and at least one light source module disposed around the QR reader device and irradiating light to the opening.

The front panel can include a light guide part through which light is delivered from the opening to the QR reading module, wherein the light guide part can have an inclined surface of which width becomes narrower from the opening, and wherein a light guide plate can be disposed on the inclined surface and convert the light from the light source module to a planar light source and delivers the light to an upper portion.

The biosensor diagnostic device can match sensor information for the biosensor cartridge inserted in the insertion hole and a reading result of the biosensor cartridge, and store the matching.

The biosensor diagnostic device can further include a cover member and an outer case surrounding the front panel and exposing the front panel by opening.

The biosensor diagnostic device can include a battery providing a power source to the plurality of functional modules, and the biosensor diagnostic device can be provided as a portable integrated device.

BRIEF DESCRIPTION OF THE DRAWINGS

The above and other objects, features and advantages of the present disclosure will be more apparent from the following detailed description in conjunction with the accompanying drawings, in which.

DETAILED DESCRIPTION OF THE EMBODIMENTS

Figure 1:
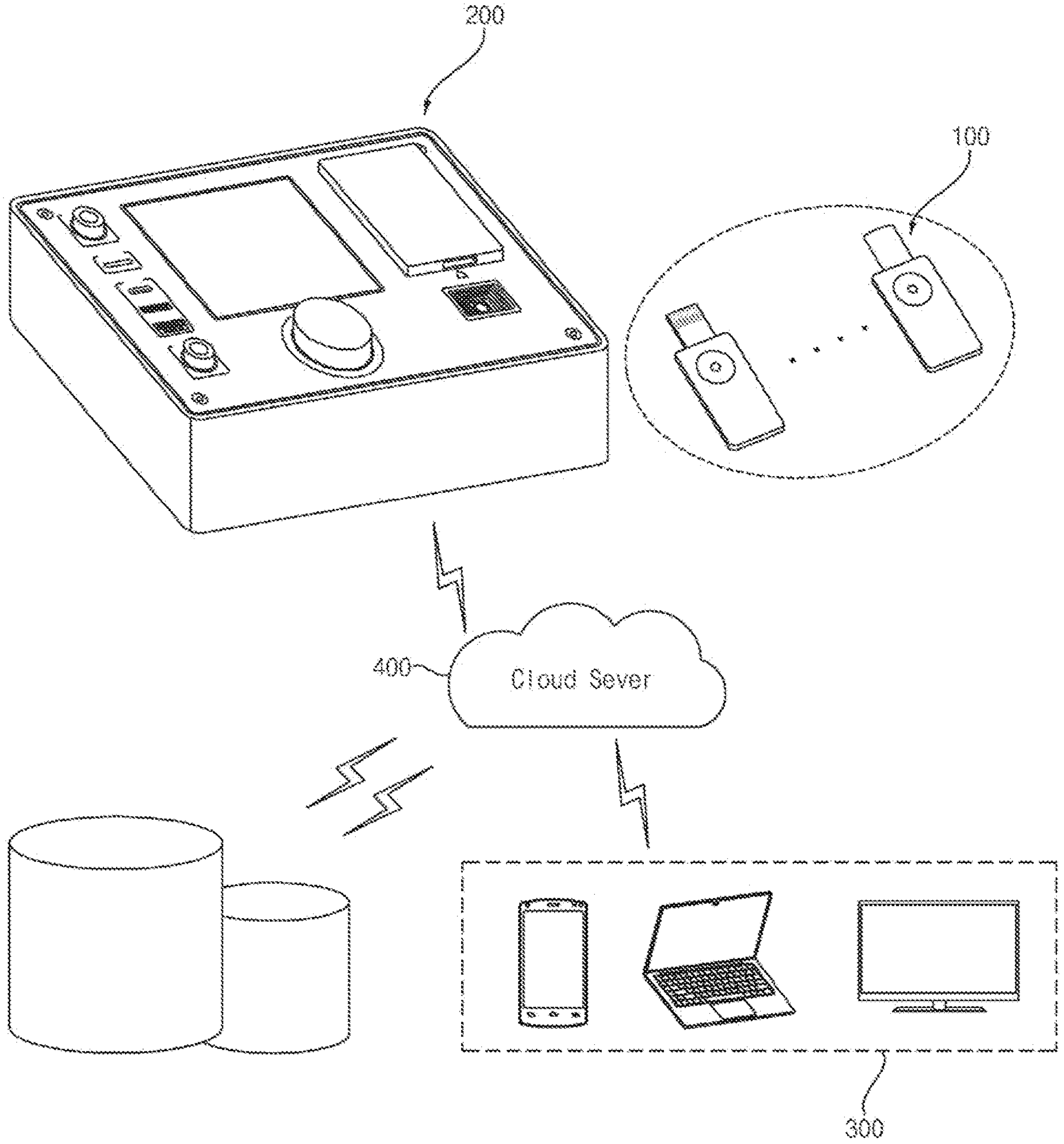
FIG. 1 is a diagram illustrating a biosensor system according to one or more embodiments of the disclosure.

Expressions referring to directions such as "front(F)/rear (R)/left (Le)/right (Ri)/up (U)/down (D)" mentioned below are defined as shown in the drawings, but, this is for the purpose of explaining an embodiment so that it can be clearly understood, and it is obvious that each direction can be defined differently depending on where standard is set.

The use of terms such as 'first, second', etc. added before the components mentioned below is only to avoid confusion of the referred components, and is irrelevant to the order, importance, or master-slave relationship between the components. For example, an embodiment including only a second component without a first component can also be implemented.

In the drawings, the thickness or size of each component is exaggerated, omitted, or schematically illustrated for convenience and clarity of description. In addition, the size and area of each component do not fully reflect the actual size or area.

In addition, angles and directions mentioned in the process of explaining a structure of the present embodiment are based on those described in the drawings. In the description of the structure in the specification, if a reference point for the angle and a positional relationship are not clearly mentioned, the related drawings can be referred to.

In the present specification, target materials are biomaterials representing a specific substrate, and are interpreted as having the same meaning as analytical bodies or analytes (e.g., a substance whose chemical constituents are being identified and measured). In the present embodiment, the target material can be an antigen. In the present specification, probe material is a biomaterial that specifically binds to a target material, and is interpreted as having the same meaning as a receptor or an acceptor. In the present embodiment, the probe material can be an antibody.

The electrochemical-based biosensor combines the analytical ability of the electrochemical method with a specificity of biological recognition, and detects a biological recognition phenomenon for a target material as a change in electrical current or electrical potential, by immobilizing or containing a material having biological specificity, i.e., probe material such as an enzyme, an antigen, an antibody, or a biochemical material, on the surface of an electrode.

Hereinafter, a biosensor system according to the present embodiment will be described with reference to FIGS. 1 and 2.

Figure 2:
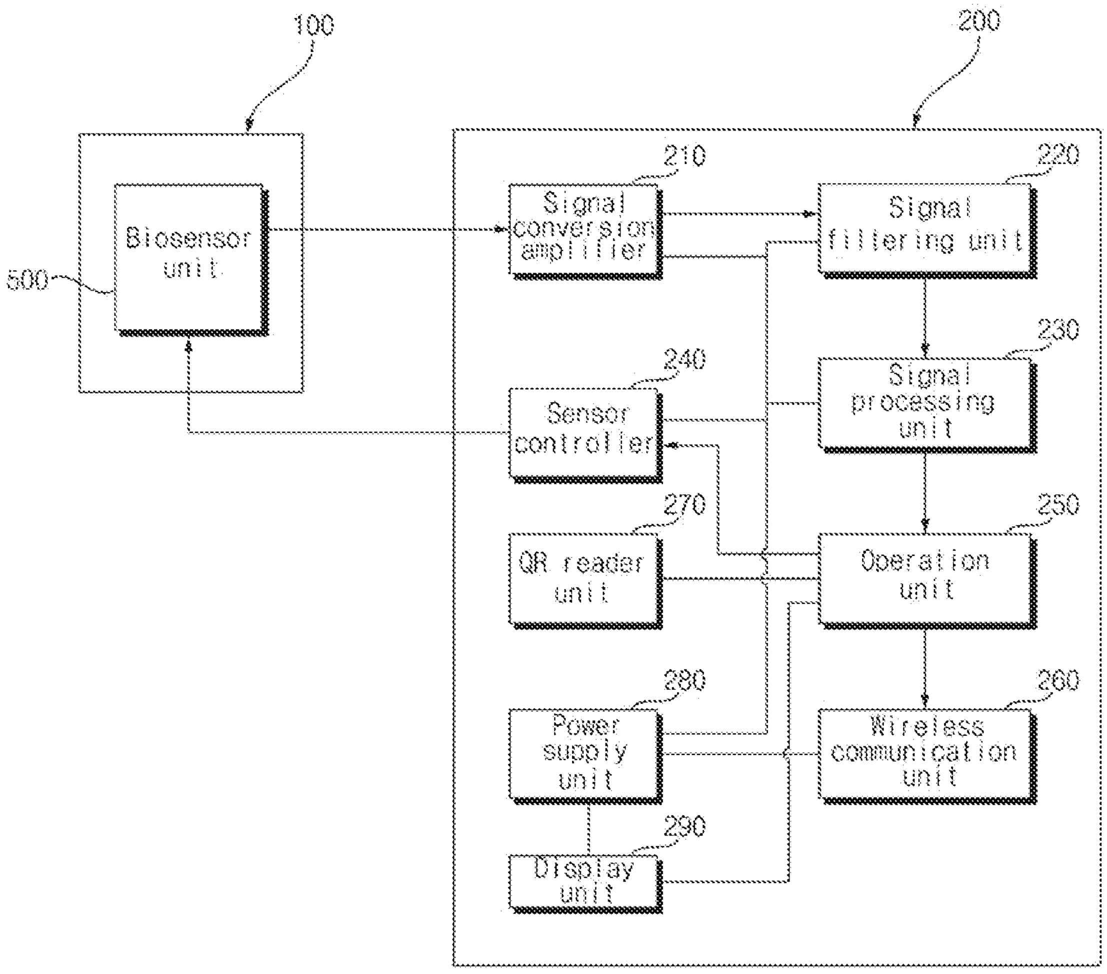
FIG. 2 is a configuration diagram of a biosensor diagnostic device and a biosensor cartridge of FIG. 1.

FIG. 1 is a diagram illustrating a biosensor system according to the present embodiment, and FIG. 2 is a configuration diagram of a biosensor diagnostic device 200 and a biosensor cartridge 100 of FIG. 1.

Hereinafter, a biosensor system according to the present embodiment will be described with reference to FIGS. 1 and 2.

FIG. 1 is a diagram illustrating a biosensor system according to the present embodiment, and FIG. 2 is a configuration diagram of a biosensor diagnostic device 200 and a biosensor cartridge 100 of FIG. 1.

Referring to FIG. 1, the biosensor system according to the present embodiment includes a biosensor diagnostic device 200, a plurality of biosensor cartridges 100, and at least one server 400.

When the plurality of biosensor cartridges 100 are inserted into the biosensor diagnostic device 200, the biosensor diagnostic device 200 reads a detection signal from the biosensor cartridge 100 to read the presence of a target material.

The biosensor diagnostic device 200 is a portable integrated diagnostic device 200 that detects a current change for the presence of a trace amount of a target material from the biosensor cartridge 100, and accordingly diagnoses a disease and delivers results of the diagnosis to a user.

To this end, the biosensor diagnostic device 200 can be provided to be portable by integrating each functional block, miniaturizing the system of functional blocks, and integrating the system into one case.

Due to its portability, the biosensor diagnostic device 200 can be moved regardless of location, regardless of the presence or absence of an external power source by mounting a battery 281 therein. In addition, the diagnostic device 200 includes a function of compensating a reproducibility and non-uniformity of a sensor by including a pre-processing process of correcting a detection signal from the biosensor cartridge 100 so as to be able to read a minute signal change.

In addition, the biosensor diagnostic device 200 includes a quick response (QR) reader that reads a QR code disposed on the rear surface of the biosensor cartridge 100 and receives environmental information for genuine product certification of the biosensor cartridge 100 to perform genuine product certification and a communication module that can transmit and receive signals for genuine product certification with an external cloud server 400.

In the biosensor diagnostic device 200, a program algorithm or application for diagnosing a disease by measuring and analyzing the detection signal from the biosensor cartridge 100 can be installed, and different algorithms are executable according to the type of each biosensor cartridge 100. That is, a plurality of different types of biosensor cartridges can be used in the biosensor diagnostic device 200, with a different algorithm being used for each different type of biosensor cartridge.

In addition, the biosensor diagnostic device 200 includes a display unit 290 for directly displaying the diagnosis result to a user, and is designed to be directly manipulated through a user interface 294, 296, 297.

The detailed configuration of the integrated biosensor diagnostic device 200 will be described later.

Meanwhile, the biosensor system includes a plurality of biosensor cartridges 100 which is inserted into the biosensor diagnostic device 200 to provide detection signals.

Each of the biosensor cartridges 100 is electrically connected to a diagnostic device 200 in which an algorithm capable of measuring and analyzing an electrical detection signal generated in a biosensor chip 500 (e.g., sensor chip) is installed.

Specifically, as shown in FIG. 1, the biosensor cartridge 100 can be inserted into and electrically connected to a cartridge insertion module 2911 of the integrated biosensor diagnostic device 200.

The biosensor cartridge 100 can accommodate the sensor chip 500 (see FIG. 6) corresponding to a biosensor unit in a housing 110, 120, and the housing 110, 120 can accommodate a circuit board 150 including a circuit pattern that extends to a connection terminal 153 that is connected to an electrode pad of the sensor chip 500 and inserted into the insertion module 2911 of an external biosensor diagnostic device 200.

The housing 110, 120 can be separated into an upper housing 110 and a lower housing 120, and the upper housing 110 and the lower housing 120 are coupled and fixed while accommodating the sensor chip 500 and the circuit board, thereby constituting a single biosensor cartridge 100.

The biosensor cartridge 100 has a connection terminal 153 for physical and electrical coupling the biosensor cartridge 100 with the biosensor diagnostic device 200. The connection terminal 153 is exposed from one end of the biosensor cartridge 100 to the outside, and a solution accommodating portion 119 (see FIG. 8) for accommodating a specimen is formed on the surface of the upper housing 110.

The solution accommodating portion 119 exposes a part of the inner sensor chip 500, and when a specimen is accommodated in the solution accommodating portion 119, the charge concentration of a channel of the sensor chip 500 is varied according to the antigen-antibody reaction of the sensor chip 500, so that the current flowing through the electrode of the sensor chip 500 varies. The varied current is read by the diagnostic device 200 through the connection terminal 153.

In this case, in order to secure the charge mobility of the sensor chip 500, a channel can be implemented with various materials, and in particular, a channel can be implemented by using graphene.

The detailed configuration of the biosensor cartridge 100 will be described in detail later.

Meanwhile, the biosensor system can include at least one server 400.

The server 400 can be a manufacturer server 400, and the server 400 can include a processor capable of processing a program. The function of the server 400 can be performed by the manufacturer's central computer (e.g., via the cloud, as known in the art).

For example, the server 400 can be a server 400 operated by a manufacturer of the biosensor cartridge 100 and the diagnostic device 200. As another example, the server 400 can be a server 400 that is provided in a building, and stores state information on devices in the building or stores content required by home appliances in the building.

The server 400 can store firmware information and diagnostic information on the diagnostic device 200, and transmit certification information on the biosensor cartridge 100 requested from the diagnostic device 200.

The server 400 in a biosensor system can be one of a plurality of cloud servers 400 of a manufacturer, and can be provided within the biosensor system while a plurality of cloud servers 400 are simultaneously included to allow access to one biosensor diagnostic device 200.

As described above, when a plurality of cloud servers 400 can simultaneously access one biosensor diagnostic device 200, the biosensor diagnostic device 200 can match the ranks with respect to the plurality of cloud servers 400, and can send a certification request sequentially from the highest priority. In this case, if a response signal is not received from the priority server 400, a certification request can be sent to the server 400 of the next priority.

The server 400 can authenticate the biosensor cartridge 100 and provide the certification result to the biosensor diagnostic device 200.

In addition, the server 400 can provide calibration data and update data for the product of a corresponding ID, and can transmit to the communicating biosensor diagnostic device 200.

The server 400 can also generate and distribute an upgraded version of a program for analysis for each biosensor cartridge 100.

To this end, the server 400 can receive history information on the manufacturing date, manufacturing conditions, sensor type, test result, etc. of the biosensor cartridge 100 of a manufacturer from a manufacturing server of a separate manufacturer.

In addition, the server 400 can periodically generate and distribute an upgraded version of a program provided to each diagnostic device 200 by receiving, accumulating, and machine learning the diagnostic result values for a corresponding product.

Meanwhile, the biosensor system of the present embodiment can further include a plurality of user terminals 300, but is not limited thereto.

When the user terminal 300 is included in the system, the biosensor diagnostic device 200 or the cloud server 400 can transmit data on the diagnosis result to the communicating user terminal 300.

To this end, a dedicated application for the user terminal 300 can be provided from the manufacturer server 400, and various processing of diagnostic data is possible by storing and executing the application in the user terminal 300.

For example, when a user is infected with the same disease for a long period of time, data processing is possible so that periodic test results can be accumulated and displayed, and the processed results can be provided to the user terminal 300 through an application. Accordingly, the user terminal 300 can be able to determine the prognosis for the disease and the expected treatment time.

The user terminal 300 can be, for example, a laptop, a smart phone, a tablet, a smart watch or the like on which an application is installed.

The user terminal 300 can communicate directly with the diagnostic device 200 or the server 400 through a network, such as a Wi-Fi network, Bluetooth network, or the like, and the diagnostic device 200 and the server 400 can also communicate directly through a network.

In this case, wireless communication technologies such as, IEEE 802.11 WLAN, IEEE 802.15 WPAN, UWB, Wi-Fi, Zigbee, Z-wave, and Bluetooth can be applied to the network, and can include a wireless communication unit 260 of each device (the user terminal 300 and the diagnostic device 200) to apply at least one or more communication technologies.

The wireless communication unit 260 can be changed depending on the communication method of other devices (the user terminal 300 and the diagnostic device 200) or the server 400 that is a target to communicate with.

As described above, in the biosensor system, the connection terminal 153 of the biosensor cartridge 100 accommodating the specimen is inserted into and electrically connected to the portable integrated biosensor diagnostic device 200 so that a detection signal is read.

The functional configuration of the biosensor diagnostic device 200 for reading the detection signal is shown in FIG. 2. Referring to FIG. 2, the biosensor diagnostic device 200 includes a plurality of function modules.

Each functional module can be individually packaged and accommodated in the case of one biosensor diagnostic device 200, and a plurality of functional modules can be packaged as one module and accommodated in a case 201, 202.

The biosensor diagnostic device 200 includes a signal conversion amplifier 210, a signal filtering unit 220, a signal processing unit 230, an operation unit 250, a wireless communication unit 260, a power supply unit 280, a display unit 290, a QR reader unit 270, and a sensor controller 240.

The signal conversion amplifier 210 receives firstly a detection signal transmitted from the biosensor cartridge 100, and converts and amplifies the current value of the detection signal so that the current value can be read by the biosensor diagnostic device 200.

The signal conversion amplifier 210 can have an analog circuit including a resistor that generates a voltage drop according to a changed current value, which is a detection signal transmitted from the biosensor cartridge 100, and can further include an amplifying circuit that receives and amplifies the voltage drop.

The amplified signal is transmitted to the signal filtering unit 220 to remove noise and then transmitted to the signal processing unit 230. The signal processing unit 230 can convert the amplified analog sensing value from which the noise has been removed into a digital value for a diagnostic operation, and can include an analog-digital converter (ADC) for this purpose.

As described above, the signal conversion amplifier 210, the signal filtering unit 220, and the signal processing unit 230 can all be implemented as a single integrated circuit chip. Such an integrated circuit chip can correspond to a cartridge insertion module 2911 in FIG. 3.

The sensor controller 240 can provide a reference voltage whose level is changed according to the control of the operation unit 250 to the connection terminal 153 of the connected biosensor cartridge 100, and the biosensor cartridge 100 receives a reference voltage having a varied level from the sensor controller 240 and flows a current value changed by a varied resistance value of channel to the connection terminal 153. The sensor controller 240 can be mounted together as a voltage level conversion circuit in an integrated circuit chip.

Meanwhile, the biosensor diagnostic device 200 includes an operation unit 250 for controlling the operation of the diagnostic device 200 and reading a received digitized detection value.

The control of the diagnostic device 200 can include a separate controller, but it is possible to simultaneously read whether a detection value is detected and control the operation of the entire diagnostic device by executing a program stored in one controller.

In this case, the operation unit 250 can be implemented as a separate integrated circuit chip, and can be mounted in a main board 255 (e.g., main circuit board 255).

The operation unit 250 can read whether there exists a target material for the detection value according to the reading program, process the result and provide the result to the display unit 290. In addition, such a reading result can be transmitted to a cloud server 400 and a user terminal 300 through a wireless communication unit 260.

The operation unit 250 can also control the operation of the diagnostic device 200 for the reading. For example, when the connection terminal 153 of the biosensor cartridge 100 is inserted into the cartridge insertion module 2911, the operation unit 250 can detect the insertion and transmit a QR reading command to the QR reader unit 270.

Accordingly, the QR reader unit 270 performs an operation for reading the QR code attached to the rear surface of the cartridge 100 inserted into the cartridge insertion module 2911, and transmits the information back to the operation unit 250.

The operation unit 250 receives the QR information, performs a certification request to the cloud server 400 accordingly, and when certification information is received from the cloud server 400 and confirmed as genuine, the operation unit 250 performs reading for the biosensor cartridge 100, and matches the reading result with the certification result of the biosensor cartridge 100 and processes it.

Accordingly, the operation unit 250 can reduce the error by minimizing the time difference of the result matching by simultaneously executing the module control of the diagnostic device 200 and the execution of the read program.

The operation unit 250 can include a memory card (e.g., an electronic data storage device, such as flash memory) as a data storage unit, a library file for diagnosing biomaterials, and an embedded system board (e.g., motherboard, mainboard) equipped with a signal processing device. For example, a memory card capable of storing output signal data is inserted into the embedded system board, and a system operating system (OS), driving program, library file for analysis, and the like are stored in the memory card. In addition, signal processing for concentration analysis of biomaterials is calculated through comparison analysis with library files in the CPU of the embedded system board, and the analyzed result is stored again in the memory card. In addition, the wireless communication unit 260 can be mounted together in such an embedded system board, but is not limited thereto.

The biosensor diagnostic device 200 includes a display unit 290 as a user interface, and the display unit 290 includes a liquid crystal display device, a touch panel, and the like to display an analyzed result detected by creating a program considering a user's convenience. Alternatively, the display unit 290 can include an LED or OLED display screen. As a user interface, it can include various types of terminals, dials, buttons, and the like.

A terminal 297, a dial 296, a button 294, and the like turn on/off the operation of the biosensor diagnostic device 200, and can be connected to the operation unit 250 to control the operation unit 250 according to a user command. That is, as a user's command is input in the interface 297, 296, 294, the diagnosis of the biosensor cartridge 100 can be started. The display unit 290 displays the progress process during the diagnosis process, and displays the diagnosis result after the completion of diagnosis.

The biosensor diagnostic device 200 includes a separate power supply unit 280 capable of applying power to a plurality of modules, and the power supply unit 280 includes a battery 281. Accordingly, it is possible to supply power to the internal module from the battery 281 by charging an external power source, and thus the device 200 can be portable.

Hereinafter, a detailed structure according to an example of the biosensor diagnostic device 200 will be described with reference to FIGS. 3 and 4.

Figure 3:
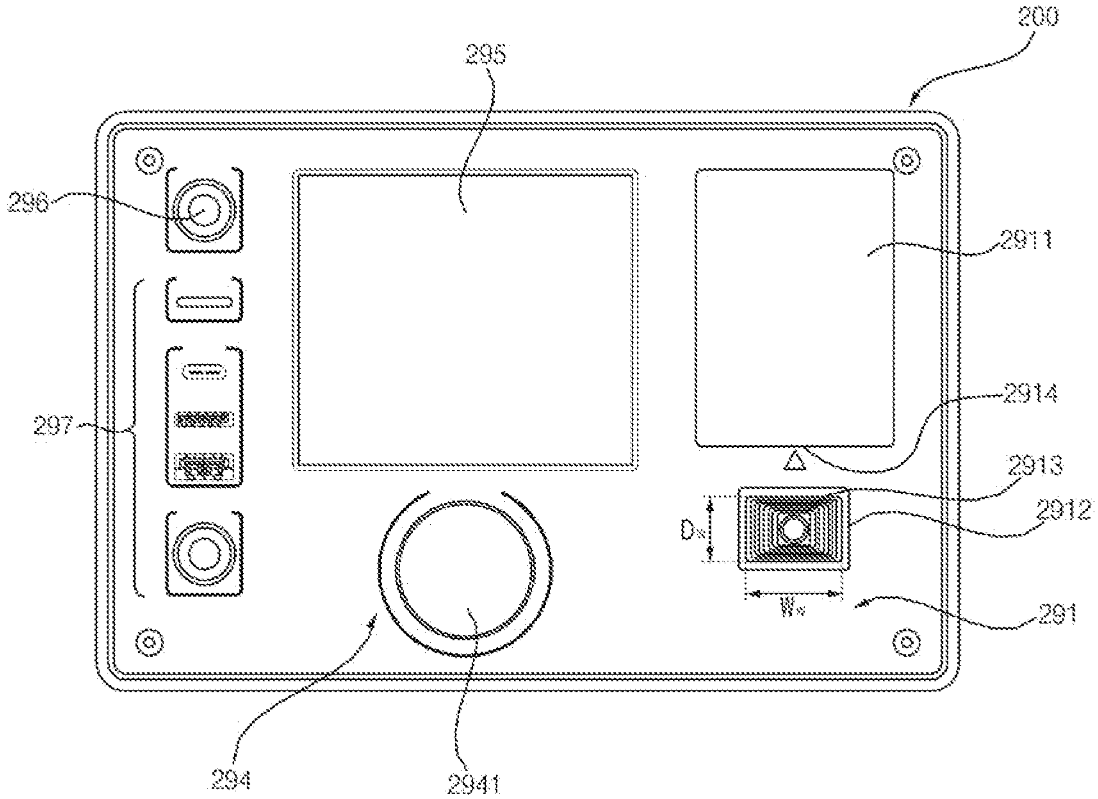
FIG. 3 is a front view of an example of the biosensor diagnostic device of FIG. 1.
Figure 4:
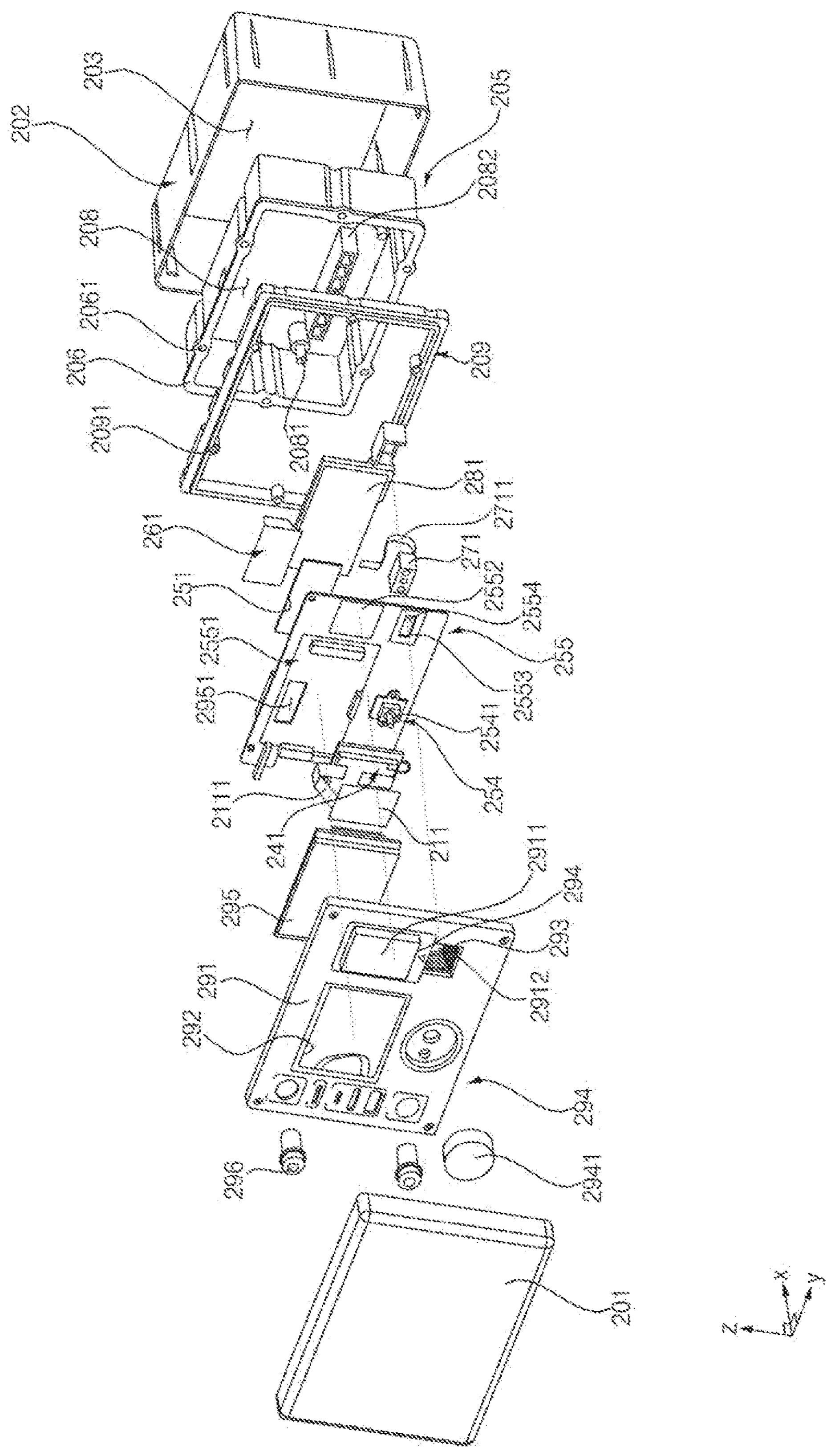
FIG. 4 is an exploded perspective view of the biosensor diagnostic device of FIG. 3.

FIG. 3 is a front view of an example of the biosensor diagnostic device 200 of FIG. 1, and FIG. 4 is an exploded perspective view of the biosensor diagnostic device 200 of FIG. 3.

Referring to FIGS. 3 and 4, the biosensor diagnostic device 200 according to the present embodiment is provided as a portable integrated device.

Here, the state of being integrated can include all states recognized as a single device in movement, disposition, and use of the diagnostic device 200. For example, the state of being integrated can mean that that it is located together inside the same case and is integrated by the same case, can mean that it is fixed by being fitted or attached to the same member and integrated by the same member, can mean that it is formed together in the same member to constitute a part of the same member, or can mean that it is wrapped or fixed together by the same member. On the other hand, it can be difficult to be considered as being integrated in the case of being connected by a separate output cable or the like.

The integrated biosensor diagnostic device 200 according to the present embodiment can include a separate inner cover 205 inside the case 201, 202. A front panel 291 is disposed to cover a plurality of modules accommodated in an accommodating portion 208 of the inner cover 205 and a front surface of the inner cover 205. The case 101 covers a portion of the front panel 291, to allow access to the plurality of modules. In this case, one of a rear case 202 and the inner cover 205 can be omitted.

In the exploded perspective view of FIG. 4, the left side is defined as a front surface and the right side is defined as a rear surface along the X axis where the plurality of modules overlap, and the Y axis and Z axis perpendicular to the X axis are defined as two axes that forms a reference plane of the front panel 291 provided to a user.

The case 201, 202 of the biosensor diagnostic device 200 according to the present embodiment can include a front case 201 and a rear case 202. The rear case 202 is formed to have an accommodating portion 203 therein, and to have a bottom surface and a side surface.

The front case 201 and the rear case 202 can be disposed to face the accommodating portion 203 while the side surfaces are in contact with each other.

The accommodating portion 203 formed by the front case 201 and the rear case 202 is changed from an open space to a closed space according to the opening and closing of the front case 201.

An outer case accommodating the front case 201 and the rear case 202 simultaneously can be further formed. The outer case can be formed in a box type as shown in FIG. 3, can have a handle formed for easy portability, and have a pedestal formed to dispose the diagnostic device 200 at a certain angle.

The bottom surfaces of the front case 201 and the rear case 202 have the same size and define the total area of the biosensor diagnostic device 200.

The bottom surface can be formed in various shapes, and the shape can be a rectangle as shown in FIG. 4, but is not limited thereto, and can be a circle, an ellipse, a rhombus, or the like.

Meanwhile, when the shape of the bottom surface is a rectangle as shown in FIG. 4, the area is a portable size, and in the case of a polygon, one side can satisfy 30 cm or less, but it is not limited thereto, and it can be further miniaturized. However, the biosensor diagnostic device 200 can have any shape, such as a rounded shape (e.g., oval or circle), etc.

The height of the side surface forming the accommodating portion 203 of the rear case 202 can be greater than the height of the side surface of the front case 201, and the inner cover 205 is formed in the accommodating portion 203 of the rear case 202.

The inner cover 205 has the same shape as the rear case 202 so that it can be inserted into the accommodating portion 203 of the rear case 202, and the bottom surface of the inner cover 205 can have a smaller area than the rear case 202, but can be fitted to minimize a space between the side surface and the bottom surface of the rear case 202 and the side surface and the bottom surface of the inner cover 205.

The inner cover 205 serves as a cover to protect the front case 201 and the rear case 202, which achieves a substantial integration, and when the case 201, 202 or when the inner cover is damaged, the inner cover 205 can be separated from the case 201, 202 and replaced. That is, the inner cover 205 can be separated from the front case 201 and the rear case 202.

In addition, since the inner cover 205 is integrated with the rear case 202, one of the two can be omitted.

A plurality of modules are accommodated inside the accommodating portion 203 of the inner cover 205.

A supporter 2081, 2082 for supporting a module while defining the position of each module can be formed on the bottom surface of the inner cover 205, and the supporter 2081, 2082 can be variously designed depending on the disposition of the inner modules.

The main board 255 is accommodated in the accommodating portion 208 of the inner cover 205.

The main board 255 can be electrically connected to internal modules for executing a plurality of functions, and as shown in FIG. 4, a display module 295 constituting the display unit 290 and the cartridge insertion module 2911 in which the signal conversion amplifier 210 and the sensor controller 240 are integrated can be disposed in the front direction of the main board 255. In addition, a control switch 2541 of the user interface of the front panel 291 can be disposed on the front surface.

An operation module 251 and a communication module 261 for controlling the operation of the control device and reading a detection signal according to a program can be disposed on the rear surface of the main board 255.

In addition, a QR reading module 271 can be disposed on the rear surface of the main board 255.

A battery 281 for applying power to the main board 255 and each of the functional modules is disposed, and the battery 281 can be disposed adjacent to the bottom surface of the inner cover 205.

Specifically, the front panel 291 includes a reference plane exposed on the front surface of the biosensor diagnostic device 200 as shown in FIG. 3.

The front panel 291 includes a first opening 292 for exposing a display module 295 that is disposed on the rear surface of the front panel 291 and displays an image on the front surface of the display module 295.

The first opening 292 can be covered with a transparent film, but is not limited thereto, and the display unit 290 of the display module 295 can be directly exposed (e.g., to the outside).

A plurality of buttons, dials, and terminals 294, 296, 297 and the like for a user interface can be disposed around the first opening 291.

The plurality of buttons, dials, terminals 294, 296, 297, etc. can be adjusted in various forms according to design. For example, as shown in FIG. 3, a control dial 2941 can be disposed in a lower side of the first opening 292, and a plurality of terminals and dials 296 and 297 can be disposed also in the left side of the first opening 292, thereby receiving operation commands directly from a user.

Meanwhile, the cartridge insertion module 2911 is disposed in the right side of the first opening 292 in the front panel 291, and in the right side of the reference plane. Alternatively, the cartridge insertion module 2911 can be disposed in the left side of the first opening 292 in the front panel 291, and in the left side of the reference plane.

The cartridge insertion module 2911 protrudes from the reference plane to the front surface, and includes a terminal portion to be electrically connected by inserting the connection terminal 153 of the cartridge in the Z-axis direction.

Accordingly, a terminal portion is formed in a side surface of the cartridge insertion module 2911, and the terminal portion can include at least one insertion hole 2914.

The insertion hole 2914 can be implemented in various ways depending on the shape of the connection terminal 153 of the cartridge. When the connection terminal 153 of the cartridge is formed in an SD card chip type, a USB type such as USB-A, USB-C type, or a PIN type, correspondingly, it can be formed to read an electrode of the connection terminal 153.

In addition, when the plurality of insertion holes 2914 are formed so as to read various types of connection terminal 153, the plurality of insertion holes 2914 can be disposed in parallel along the X-axis direction in the side surface of the insertion module 2911.

A second opening 293 for exposing the QR reading module 271 is disposed in the lower side of the insertion module 2911.

The second opening 293 is formed in a position aligned with the rear surface of the housing 101 of the cartridge 100 in the X-axis direction in a state in which the connection terminal 153 of the cartridge is inserted into the insertion hole 2914 of the cartridge insertion module 2911.

The second opening 293 can be covered with a transparent film, and the second opening 293 can have a rectangular shape, but an area of the second opening 293 can be smaller than that of the first opening 292. Further, the second opening 293 can have any shape corresponding to a shape of the QR reading module 271 or the QR area 2553.

The second opening 293 serves as a passage through which the QR reading module 271 disposed on the rear surface reads the QR code of the cartridge 100 that is placed on the front surface of the biosensor diagnostic device 200. In the second opening 293, a light guide part 2912 protruding from the rear surface of the front panel 291 to form a sidewall of the second opening 293 in order to maintain a distance between the QR reading module 271 and the cartridge 100 is formed.

The light guide part 2912 can serve as an illumination for photographing of the QR reading module 271 while maintaining the distance of the QR reading module 271. That is, the light guide part 2912 can include a light guide plate formed on a sidewall of the second opening 293 and can shine light towards the biosensor cartridge to allow the QR reading module 271 to read a barcode.

A main board 255 in which each module is mounted is disposed on the rear surface of the front panel 291, and the main board 255 can also have a shape similar to the bottom surface of the inner cover 205.

The main board 255 is divided into a display area 2551 in which the display module 295 is disposed in correspondence with the area division of the front panel 291, a cartridge area 2552 corresponding to the cartridge insertion module 2911, a QR area 2553 corresponding to the second opening 293, and a control area 254 corresponding to the button and the dial for a user interface.

The main board 255 is a circuit board on which a circuit is patterned on the front and rear surfaces, and a connection terminal or a connector for electrical connection is disposed in each area. Each functional module can be integrated on the main board 255 after connecting the connection terminal of the board and connector and the connection terminal of each module or connector while being physically fixed in a defined area.

As shown in FIG. 4, a terminal module 241 in which the signal conversion amplifier 210, the signal filtering unit 220, and the sensor controller 240 are integrated is mounted in the cartridge area 2552 of the main board 255 corresponding to the cartridge insertion module 2911. The terminal module 241 can be connected to a insertion hole module 211 into which the connection terminal 153 of the cartridge is inserted by a flexible printed circuit board FPCB 2111, and unlike this, can be implemented as a single (e.g., unitary) component.

In addition, the display module 295 can be an LCD or LED panel module, or any known type of display panel disposed in the display area 2551, and a terminal opening 2951 can be formed in the main board 255 in order to connect the operation module 251 on the rear surface of the main board 255 with the battery 281.

The operation unit 250 and the communication module 261 can also be connected to the main board 255 through a connector at the rear surface of the main board 255, but the disposition on the main board 255 is not limited thereto.

Meanwhile, the QR reading module 271 that reads a QR code through a QR opening 2554 formed in the QR area 2553 is disposed on the rear surface of the main board 255, and the QR reading module 271 is also electrically connected to the main board 255 through the flexible printed circuit board FPCB 2711 to receive power and control signals. That is, the QR reading module 271 can include the FPCB 2711 to electrically connect the QR reading module 271 to the main board 255.

A side frame 209 is formed for the disposition and fixing of such modules. The side frame 209 fixes the inner cover 205 and the front panel 291, and the inner cover 205 is fixed to the side frame 209 through a screw hole 2061 (or a plurality of screw holes 2061) extended from one end portion 206 of the side surface. Further, the side frame 209 is provided with multiple screw holes 2091 that overlap the screw holes 2061 of the inner cover 205. Fasteners, such as screws or bolts, pass through the screw home 2091 of the side frame 209, then are fixed to the screw holes 2061 of the inner cover 205. Each module is fixed at a specific position on the main board 255 through a plurality of other fixing parts, the main board 255 is physically fixed by coupling a screw and a screw hole between a plurality of fixing protrusions 2081 and 2082 protruding from the bottom surface of the inner cover 205 and the front panel 291.

Each module and component disposed therebetween is fixed by fixing the main board 255, the front panel 291, and the inner cover 205, and an electrical connection is maintained without being shaken during movement.

In addition, the front panel 291 and the inner cover 205 are fixed together through the screw hole and the screw of the side frame 209 to be integrated. Fixing and assembling of each component proceeds by the screw hole and the screw, thereby making it easy to disassemble and reassemble.

The front case 201, the rear case 202, the inner cover 205, and the front panel 291 can be formed of a resin, such as polycarbonate or a plastic for portability.

The biosensor diagnostic device 200 is, as shown in FIG. 3, provided to a user by exposing the front panel 291 in a form of having a space for accommodating a plurality of modules therein, and various external cases can be applied.

In particular, in the reference plane of the front panel 291 provided to a user as shown in FIG. 3, a screen of the display module 295 is provided, and various buttons and dials for a user interface are provided. In particular, a power button, a plurality of control buttons, and a USB terminal (or other terminal device) can be provided. In addition, the cartridge insertion module 2911 is provided to one side of the display module 295, and the connection terminal 153 is inserted into the insertion hole 2914 parallel to the reference plane of the panel 291, so that diagnosis of the biosensor cartridge 100 is possible.

Hereinafter, the biosensor cartridge 100 applied to the present embodiment will be described with reference to FIGS. 5 to 7.

Figure 5A:
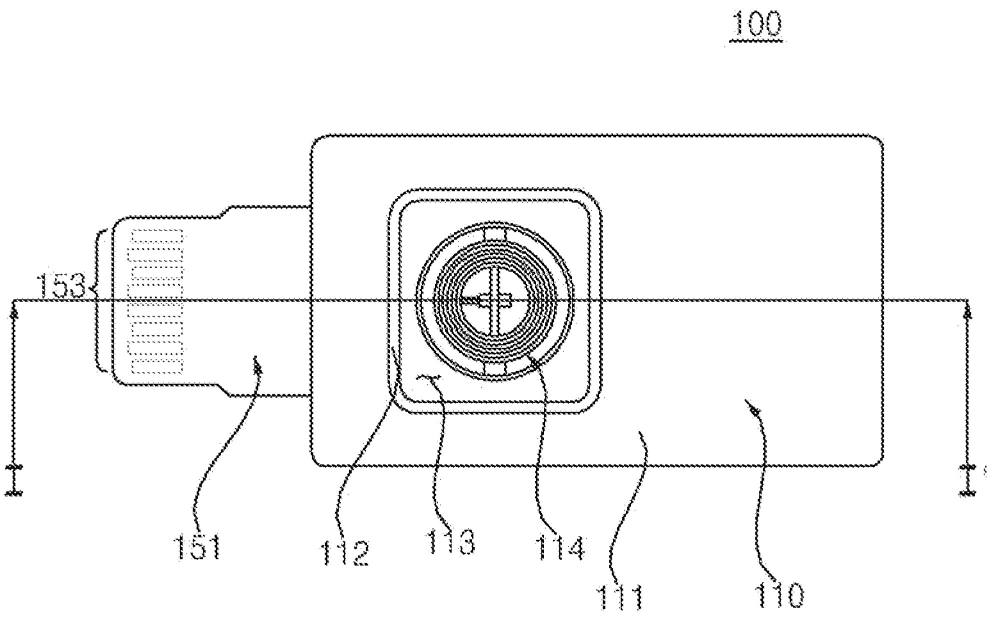
FIGS. 5A and 5B are respectively top and rear views of an example of the biosensor cartridge of FIG. 1.
Figure 5B:
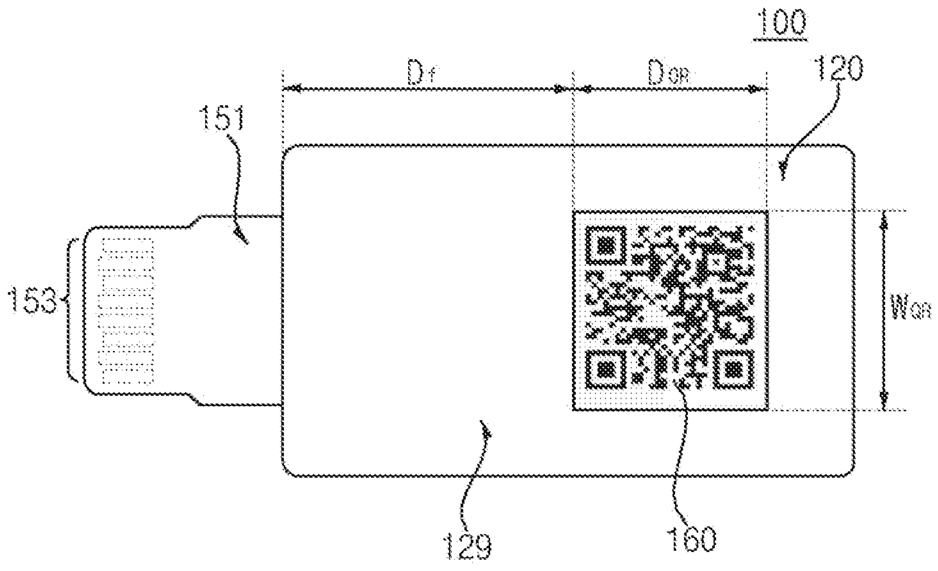
Figure 6:
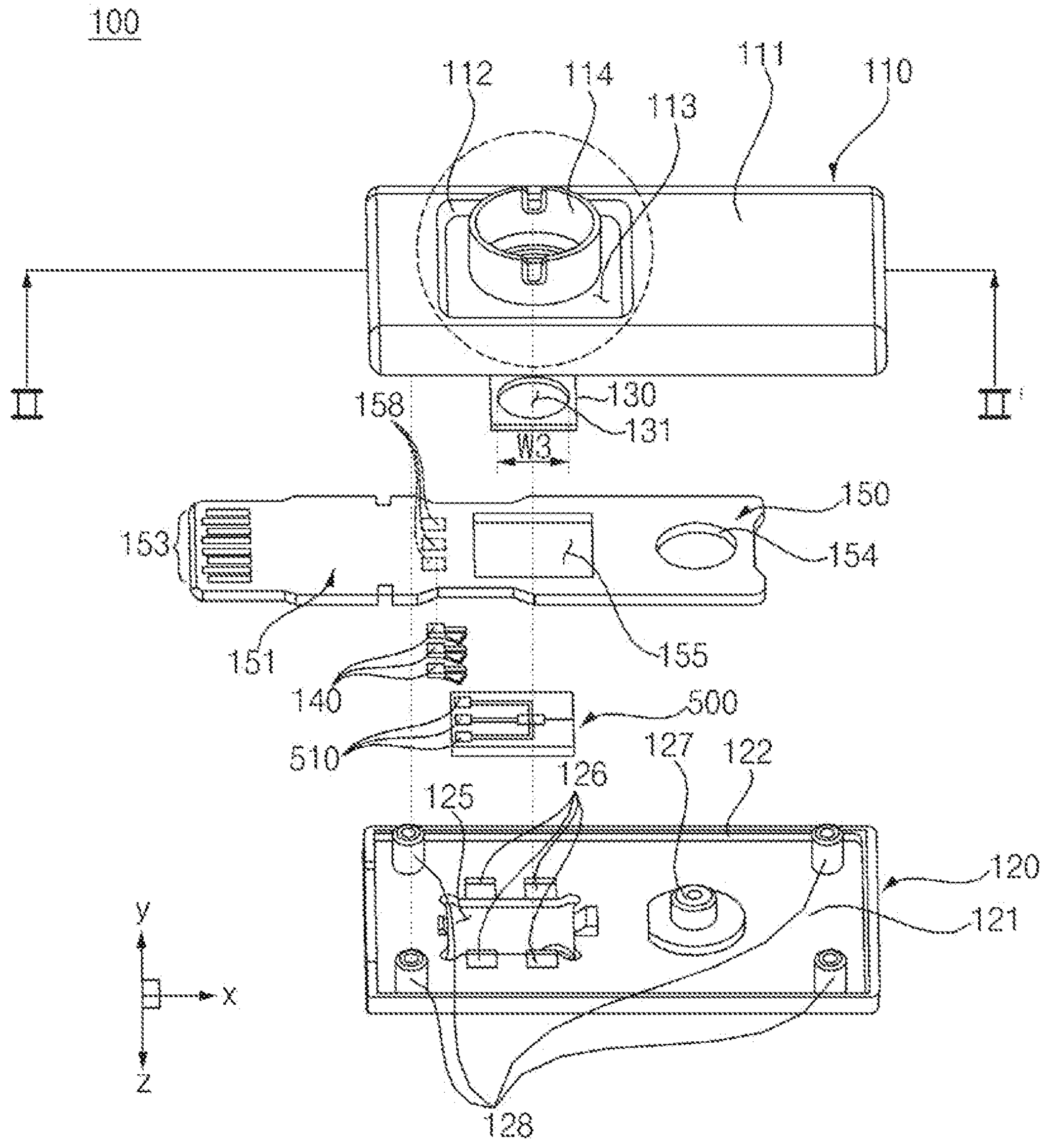
FIG. 6 is an exploded perspective view of an example of the biosensor cartridge of FIG. 1.
Figure 7:
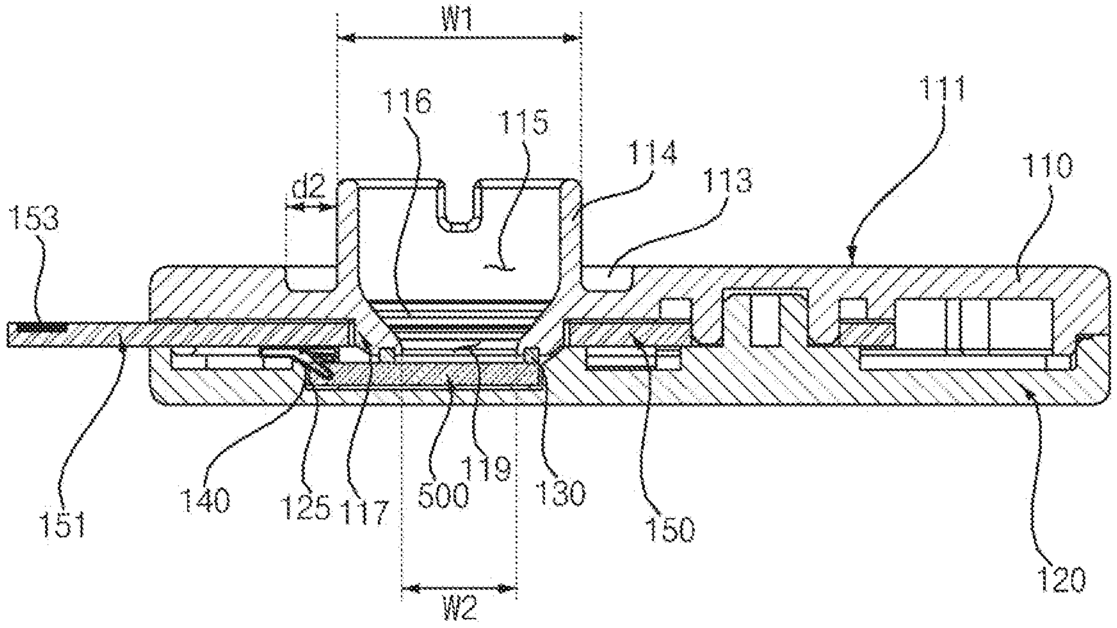
FIG. 7 is a cross-sectional view of the biosensor cartridge of FIGS. 5 and 6 taken along lines I-I' and FIG. 8 is an exploded perspective view of another example of the biosensor cartridge of FIG. 1.

FIGS. 5A and 5B are top and rear views of an example of the biosensor cartridge 100 of FIG. 1, FIG. 6 is an exploded perspective view of an example of the biosensor cartridge 100 of FIG. 1, and FIG. 7 is a cross-sectional view of the biosensor cartridge 100 of FIGS. 5 and 6 taken along lines I-I' and II-II'.

FIGS. 5A to 7, the biosensor cartridge 100 according to the present embodiment accommodates a sensor chip 500 that generates an electrical detection signal according to (e.g. depending on) a target material, and has a structure of including a connection terminal 153 capable of transmitting the detection signal to an external diagnostic device 200.

Specifically, the biosensor cartridge 100 is formed of a bar type housing 110, 120, a partial surface 151 of the circuit board 150 protrudes from the end surface of the side surfaces of the housing 110, 120, and a connection terminal 153 that is inserted into the external diagnostic device 200 and transmits the detection signal is formed on the partial surface 151 of the protruding circuit board 150.

The biosensor cartridge 100 includes housing 110, 120, a sensor chip 500, and a circuit board 150.

The circuit board 150 is also formed in a bar type, and has one end where a connection terminal 153 is formed so that the connection terminal 153 of the circuit board 150 is coupled to be exposed to the outside of the housing 110, 120, thereby forming the entire shape of cartridge 100.

Specifically, the housing 110, 120 includes a lower housing 120 and an upper housing 110.

The lower housing 120 includes a bar-type bottom surface 121 (e.g., a planar shaped surface or a rectangular shape surface that is planar) and a side surface 122 surrounding the bottom surface 121. The bottom surface 121 includes a plurality of coupling protrusion 127, 128 protruding toward the upper housing 110, and the coupling protrusions 127, 128 are fitted with coupling grooves of the upper housing 110 so that the upper and lower portions of the housing 110, 120 are coupled and integrated. The lower housing 120 can include four coupling protrusions 128 positioned at corners of the lower housing 120, which are coupled to corresponding grooves of the upper housing 110 which are located at corners of the upper housing 110. The coupling protrusion 127 (e.g., substrate protrusion) can be from the other coupling protrusions 128 (e.g., corner coupling protrusions 128). Alternatively, more than four coupling protrusions 127 can be formed and the coupling protrusions can be equally spaced around a periphery of the lower housing 120.

A substrate protrusion 127 defining a position while fixing the circuit board 150 toward the upper housing 110 is formed on the bottom surface 121 of the lower housing 120, and a plurality of sensor protrusions 126 defining a chip area 125 in which the sensor chip 500 is disposed are formed in one side of the lower housing 120, the one side facing the upper housing 110.

The sensor protrusion 126 is disposed to correspond to the size of the sensor chip 500 so as to define a chip area 125 in which the sensor chip 500 is disposed, and is formed to have a certain elasticity (e.g., predetermined elasticity) so that the sensor chip 500 can be fitted. Each sensor protrusion 126 has a protruding structure having an inclination toward the chip area 125 so that it is not damaged by the edge of the sensor protrusion 126 when the sensor chip 500 is mounted. However, since the sensor protrusion 126 does not electrically connect the sensor chip 500, it can be implemented in various forms, and can be formed as a rail structure for sliding coupling in addition to fitting.

A sensor chip 500 is disposed in the chip area 125.

The sensor chip 500 is a semiconductor-based biosensor, and is divided into a sensor area 540 (see FIG. 10) that reacts according to a target material in the specimen through contact with the specimen, and a pad area 510 for transmitting a detection signal generated according to the sensor area 540 to the circuit board 150.

The pad area 510 can be patterned to be disposed in one side of the sensor chip 500 as shown in FIG. 6, and accordingly, the electrical connection between the circuit board 150 and the sensor chip 500 is performed in the pad area 510.

The sensor chip 500 can have different sizes depending on the size of the cartridge, for example, can have a rectangular shape of 8 mm*6 mm, or can have a square shape of 6 mm*6 mm. The size of the sensor chip 500 can be variously implemented according to the performance of the sensor chip 500 or the purpose of the sensor chip 500.

The detailed structure of the sensor chip 500 will be described in detail later.

The circuit board 150 is disposed on the sensor chip 500.

The circuit board 150 can be provided as a rigid board like a printed circuit board (PCB) board, and the sensor chip 500 is electrically/physically bonded to the lower portion.

The circuit board 150 includes a sensor opening 155 through which a sensor area 540 of the sensor chip 500 is exposed, and the sensor opening 155 has a size smaller than that of the sensor chip 500. In addition, the opening 155 can have a size corresponding to the sensor area 540 of the sensor chip 500, and has a size to expose the sensor area 540.

The circuit board 150 further includes a protrusion hole 154 through which the substrate protrusion 127 of the lower housing 120 penetrates to fix the circuit board 150 to the lower housing 120, and accordingly, the circuit board 150 and the lower housing 120 are fixed.

The circuit board 150 can be implemented by a plurality of circuit patterns patterned on a base member (not classified by reference numerals, denoted by 150 in the drawing) as the deposition structure thereof, and an insulating layer covering the circuit pattern.

Accordingly, the number of connection terminal 153 on the front surface of the circuit board 150 can be equal to or greater than the number of pads of the sensor chip 500.

For example, when the sensor chip 500 has three pads, the number of the connection pads 158 of the circuit board 150 also satisfies three, and the number of the connection terminal 153 satisfies three or more.

The connection terminal 153 further includes terminals not electrically connected to each connection pad 158 and can be used as a terminal for electrostatic discharge (ESD blocking.

Meanwhile, the circuit board 150 includes a plurality of coupling grooves, and the plurality of coupling grooves are formed to be able to fit while specifying a position when the upper housing 110 and the lower housing 120 are coupled.

Meanwhile, the upper housing 110 has a structure where the upper surface 111 and the rear surface are different from each other as shown in FIG. 6.

The upper housing 110 faces the lower housing 120 and is coupled to the lower housing 120 and serves as an upper case capable of accommodating the circuit board 150 and the sensor chip 500 therein. In addition, an accommodating portion 119 exposing the sensor area 540 of the sensor chip 500 is formed in the upper housing 110 to accommodate a test target specimen.

The upper housing 110 is formed to have rigidity that can firmly support the connecting member 140 by pressing the connecting member 140 with a certain force. The connecting member 140 can be formed in plurality and can be conductive tabs (e.g., metal tabs) for connecting the connection pad 158 disposed on the circuit board 150 with the pads 511 of the sensor chip 500.

The upper housing 110 and the lower housing 120 can be configured to surround the surfaces of the sensor chip 500 and the circuit board 150 to protect the sensor chip 500 and the circuit board 150 from the outside. At this time, when the upper housing 110 and the lower housing 120 are coupled, an opening through which the connection terminal 153 of the circuit board 150 protrudes is formed in one side (e.g., a first side) of the side surface, e.g., in a cross-section, so that the connection terminal 153 is exposed to a cross-section, and is inserted into the insertion hole 2914 of the external diagnostic device 200 as the connection terminal 153 of the cartridge. The strong coupling between the upper housing 110 and the lower housing 120 can prevent the specimen provided to the sensor chip 500 from being leaked into the inside of the housing 110 and 120 through the accommodating portion 119.

The accommodating portion 119 for exposing the sensor area 540 of the sensor chip 500 and accommodating a specimen is formed on the upper surface 111 of the upper housing 110. The accommodating portion 119 is a space for inducing a reaction with the exposed sensor area 540 by accommodating a test target specimen in a fluid state, e.g., in a liquid state, and the accommodating portion 119 forms a conical channel whose diameter becomes narrower as it approaches the sensor area 540 from the upper surface 111. The area of the accommodating portion 119 closest to the sensor area 540 is called the distal end, and the area furthest from the sensor area 540, which is opposite to the distal end, is considered the opening or outermost area. The distal end has a diameter W2 that is smaller than the diameter W1 of the opening/outermost area.

The accommodating portion 119 is formed to have an inclined surface 116 such that a diameter w1 of the opening of the upper surface is larger than a diameter w2 of the opening at the distal end of the accommodating portion 119.

At this time, an inclination angle of the inclined surface 116, which is the angle of the inclined surface 116 with respect to the horizontal direction (x-axis) in which the sensor chip 500 is placed, when viewed from the cross section in FIG. 7—can be uniform, but the inclined surface 116 can have an inflection point.

That is, the inclination angle can increase as it approaches the sensor area 540, and it forms a verticality (e.g., is substantially vertical) in the outermost area closest to the sensor area 540, so that the accommodating portion 119 can be changed to a cylindrical passageway.

As described above, since the accommodating portion 119 has the inclined surface 116, a concave groove having a depth that is a height from the upper surface of the upper housing 110 to the sensor area 540 is formed. A specimen is collected in the groove to induce a reaction with the probe material in the sensor area 540.

Meanwhile, the accommodating portion 119 further includes a guard 114 for preventing the specimen of the accommodating portion 119 from flowing to the outside as shown in FIGS. 5A to 9. The guard 114 can be formed in a cylindrical shape, and is formed to surround the opening of the upper surface 111 of the upper housing 110 and protrude upward (in the y-axis) from the upper surface 111.

Accordingly, the diameter w1 of the guard 114 can be the same as the diameter of the opening of the upper surface 111.

A guard groove 113 of a certain depth is formed on the upper surface 111 of the upper housing 110 while surrounding the accommodating portion 119. The guard groove 113 prevents the specimen overflowing from the accommodating portion 119 from flowing out of the housing 110, and is formed to be recessed by a certain depth from the upper surface 111.

The guard groove 113 can be formed in a circular shape identical to the shape of the guard 114, but can be formed in a rectangular shape having a minimum distance d2 or more from the guard 114 as shown in FIGS. 6 and 7. The guard groove 113 includes a vertical wall 112 defining an outer periphery of the guard groove 113.

As described above, the accommodating portion 119, where the specimen and the sensor area 540 contact each other, firstly has a concave cup shape to accommodate the specimen and provides a space where the target material of the specimen and the probe material of the sensor area 540 react with each other. In addition, the accommodating portion 119 forms a guard 114 surrounding the opening of the upper surface 111 to secure the amount of the specimen (e.g., a predetermined amount) by accommodating the overflowing specimen secondarily, and to prevent the risk of exposing the specimen to the outside.

In addition, tertiarily, the guard groove 113 is formed around the guard 114 to accommodate overflow of the specimen past the guard 114 when the specimen overflows the guard 114 or flows to the outside of the guard 114, thereby preventing the specimen, that can contain hazardous substances, from exposing to the outside.

Thus, the test can be safely performed by changing the shape of the accommodating portion 119 for accommodating the specimen in the upper housing 110.

Meanwhile, the rear surface of the upper housing 110 can include an inclined portion along the inclined surface 116 of the accommodating portion 119.

Accordingly, as shown in FIG. 7, the sensor area 540 of the sensor chip 500 is exposed upward by the sensor opening 115 of the circuit board 150, and the lower opening of the accommodating portion 119 aligns with the exposed sensor area 540.

At this time, the opening 115 of the circuit board 150 is fitted to surround the rear surface of the inclined surface 116 of the accommodating portion 119, thereby fixing the positions of the circuit board 150 and the upper housing 110.

In addition, to this end, the rear surface of the inclined surface 116 of the accommodating portion 119 is formed to have a vertical step 117 in an area where it meets the opening 115 of the circuit board 150.

Accordingly, the circuit board 150 is firstly fixed while the step 117 of the rear surface of the accommodating portion 119 and the sensor opening 115 of the circuit board 150 are fitted, and is secondarily fixed while the fixing protrusion 127 of the lower housing 120 and the protrusion hole 154 of the circuit board 150 are coupled, so that the position is specified.

Meanwhile, a sealing part 130 can be further formed between the upper housing 110 and the sensor area 540.

The sealing part 130 is formed as a separate element as shown in FIG. 6, and is coupled and compressed at the time of the housing 110, 120 coupling, thereby preventing the specimen from flowing to the outside of the sensor area 540.

In this case, the sealing part 130 can have a sealing opening 131 having a diameter w3 larger than the diameter w2 of the rear opening of the accommodating portion 119 as shown in FIG. 6, and the rear opening and the sealing opening 131 can be disposed to have a concentric circle. Accordingly, when assembling, as shown in FIG. 7, the sealing part 130 is disposed outside the lower opening of the accommodating portion 119 to form a concave groove. The sealing part 130 can be elastic, and formed of a rubber, fluorinated rubber, silicon, neoprene, nitrile, polyvinyl chloride (PVC), thermoplastic polyurethane, polytetrafluorethylene and the like.

This is designed to avoid danger that the sealing part 130 is pushed to the sensor area 540 by the compression of the sealing part 130 and covers the sensor area 540 in contact with the specimen, as a tolerance is set when the sealing part 130 is compressed.

As described above, it is possible to ensure the sealing of the specimen while securing the area of the sensor area 540 by adjusting the size of the sealing opening 131 of the sealing part 130 and the opening size of the accommodating portion 119.

Meanwhile, the sealing part 130 can be a closed cell type waterproof pad having elasticity, but is not limited thereto.

The upper housing 110 and the lower housing 120 can be manufactured by molding (e.g., injection molding, compression molding, transfer molding, and the like). In this case, the upper housing 110 and the lower housing 120 can be made of at least one of Polymethyl Methacrylate, Polycarbonate, Cyclic olefine copolymer, Polyethylene sulfone and polystyrene, or a combination of at least two material thereof. However, the material of the housings 110, 120 is not limited thereto, and can be made of Polydimethylsiloxane, which is silicone based organic polymer.

Meanwhile, the connection pad 158 formed on the rear surface of the circuit board 150 is formed in the same number as the pad 511 of the sensor chip 500, and a connecting member 140 is disposed for electrical and physical connection between the connection pad 158 of the circuit board 150 and the pad 511 of the sensor chip 500.

As shown in FIG. 6, the connecting member 140 can be formed separately for each pad 158, and can be formed as a clip-type elastic contact piece. Such a connecting member 140 can be a C-clip or a spring terminal.

Each connecting member 140 can include a first surface in contact with the connection pads 158 of the circuit board 150 and a second surface configured to be elastically deformable by being bent in the length direction of the first surface from one side surface of the first surface.

The first surface is formed to have a certain length and is in contact with the connection pads 158 of the circuit board 150, and the second surface is in contact with the pad 511 of the lower sensor chip 500 and elastically deformed.

In the connecting member 140, when a bending portion, which is bended part between the first surface and the second surface, is elastically deformed, and pressure is exerted in upper and lower directions between a lower part of the first surface and an upper part of the second surface, the first surface contacts the connection pad 158, and the second surface contacts the pad 510 of the sensor chip 500.

To this end, in the state where the connection pad 158 of the circuit board 150 and the first surface are in contact with each other through welding or soldering, when the circuit board 150 is disposed in the lower housing 120 in which the sensor chip 500 is disposed, a bending portion is elastically deformed as pressure is applied vertically to the connecting member 140 by assembling the upper housing 110 and the lower housing 120.

Thus, the second surface is in contact with the pad 510 of the sensor chip 500 to maintain a conducting state, so that physical coupling and electrical coupling occur simultaneously.

As described above, since the probe material in the sensor chip 500 is not exposed to high temperature in a bonding process by performing electrical connection of the sensor chip 500 with the circuit board 150 without a separate bonding process, it is possible to prevent a problem that protein modification occurs.

That is, in the presence of probe material vulnerable to heat due to the characteristics of the biosensor, the characteristics of the probe material can be maintained by excluding a heating process, and electrical connection between the sensor chip 500 and the circuit board 150 becomes possible.

Meanwhile, on the rear surface 129 of the lower housing 120 of the biosensor cartridge 100, i.e., the rear surface 129 of the cartridge 100 exposed to the outside, a QR label 160 including a QR code in which sensor information including a product ID and a manufacturing serial number for genuine product certification of the biosensor cartridge 100 is stored is attached.

The QR label 160 can have a rectangular shape, of which a width is 11 to 13 mm, and a length is 14 to 16 mm. Preferably, the QR label 160 can have a size of 12*15 mm, and the size of the QR label 160 can have a value smaller than 25 mm*18 mm, which is a size of the second opening 293 of the diagnostic device 200.

The QR label 160 can be attached to a center area of the rear surface 129 of the lower housing 120 such that the rear surface 129 of the lower housing 120 of the cartridge 100 can be aligned on the second opening 293, which is the QR opening, when the cartridge 100 is coupled with the diagnostic device 200. A distance between a side end part to which the connection terminal 153 of the lower housing 120 is protruded and the QR label 160 satisfies 11 to 12 mm. Accordingly, since this has a value smaller than the distance between the insertion hole 2914 of the diagnostic device 200 to the center of the second opening 293, the QR label 160 is not deviated to the exterior of the second opening 293, but aligned therewith.

The QR code can include all sensor information for genuine product certification. As an example, it can include sensor chip 500 information and cartridge information as well as the product ID and manufacturing serial number. The information of the sensor chip 500 can include probe material activated in the sensor chip 500, a disease to be diagnosed, a manufacturing date, a manufacturing location, and a manufacturing serial number of the sensor chip 500. In addition, the cartridge information can include an assembly date, a test date, and a sensor ID of the biosensor cartridge 100.

The stored QR code is read from the QR reading module 271 of the diagnostic device 200 at the same time when it is inserted into the diagnostic device 200, and a process for genuine product certification can be performed with the cloud server 400.

The biosensor cannot determine whether it is an imitation or not. Even if it is genuine, sensor errors are often found or decided from accumulated test data after manufacturing and sales. Therefore, a process of classifying the biosensor cartridge 100 in which an error has occurred is required before the test proceeds.

In the case of the biosensor cartridge 100, it is possible to check an error including a current risk to a corresponding type of the biosensor cartridge 100 through such a certification procedure.

The biosensor cartridge 100 according to the present embodiment does not include a separate memory chip for storing sensor-specific information for such a certification procedure.

When such a memory chip is separately included, the size of the circuit board 150 increases, and the size of the housing 110, 120 increases according to the size of the circuit board 150. In addition, as the circuit of the circuit board 150 becomes complicated, the number of pins used in the connection terminal 153 increases, thereby causing problems in miniaturization and cost of the cartridge 100.

Like the biosensor cartridge 100 according to the present embodiment, by attaching a QR label 160 on which a QR code is printed to the rear surface of the housing, such a memory chip, can be replaced, and the time difference between reading of the sensor result and certification can be minimized by reading the QR code almost simultaneously with the coupling of the cartridge 100 and the diagnostic device 200.

Such a QR code can be prevented from being arbitrarily attached and detached by attaching it as a security label (e.g., QR label 160) such as a VOID label on the rear surface of the lower housing 120.

In such a biosensor cartridge 100, in a state in which the sensor chip 500 is placed in the lower housing 120, the upper housing 110 coupled to the circuit board 150 to which the connecting member 140 is attached is pressed for assembling with the lower housing 120, so that the sensor chip 500 and the circuit board 150 are physically and electrically attached and fixed.

Figure 8:
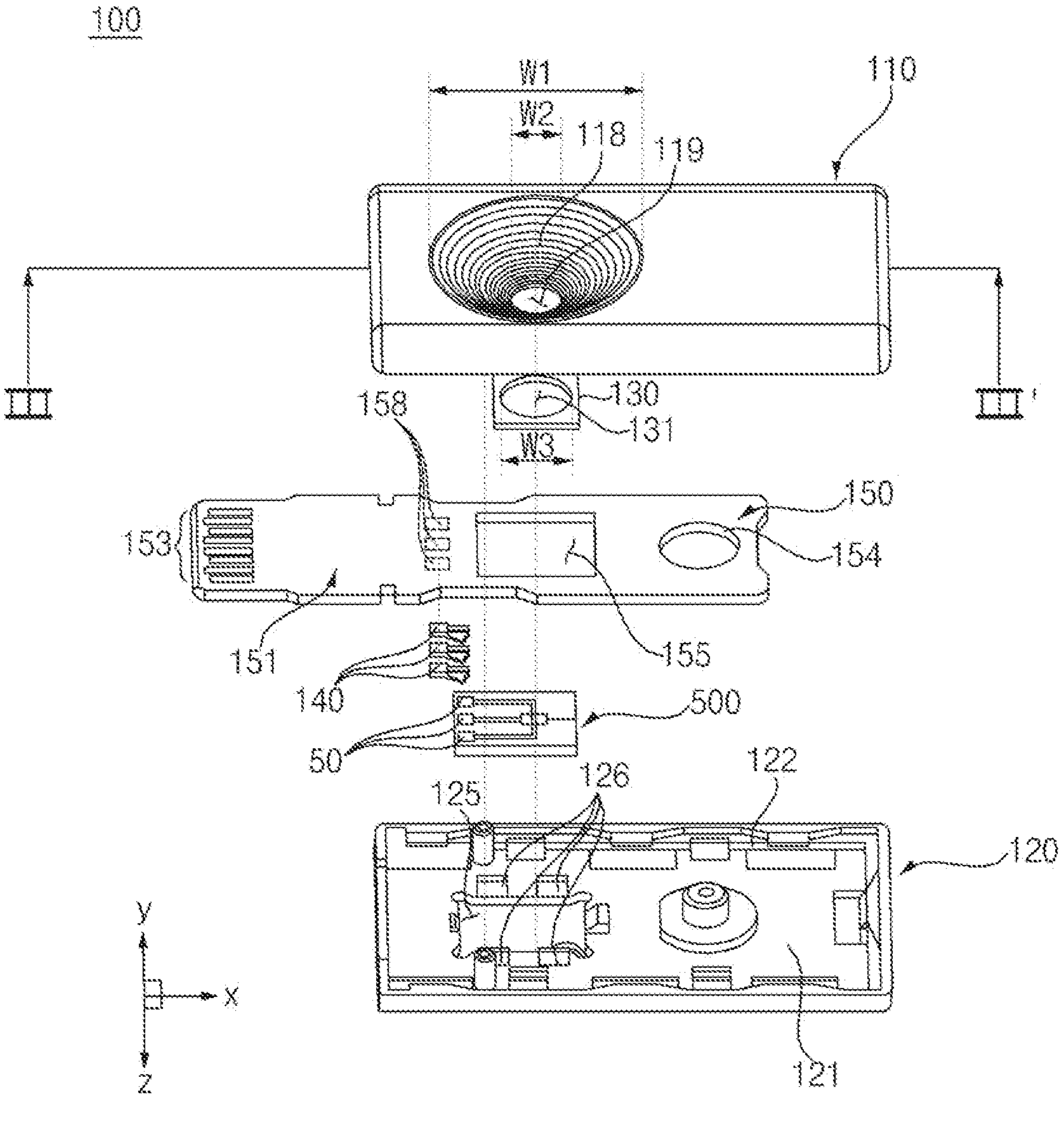
Figure 9:
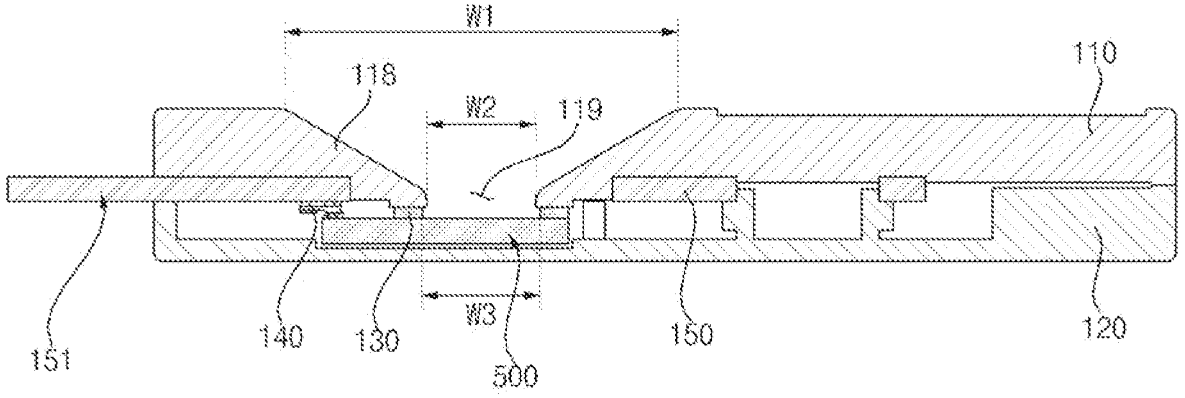
FIG. 9 is a cross-sectional view of the biosensor cartridge of FIG. 8 taken along line III-III'.

Such a biosensor cartridge 100 can be changed to a configuration shown in FIGS. 8 and 9.

FIG. 8 is an exploded perspective view of another example of the biosensor cartridge 100 of FIG. 1, and FIG. 9 is a cross-sectional view of the biosensor cartridge 100 of FIG. 8 taken along line III-III'.

In the biosensor cartridge 100 of FIGS. 8 and 9, since the configuration of the lower housing 120, the sensor chip 500, and the circuit board 150 is the same as that of the biosensor cartridge 100 of FIGS. 6 and 7, and the attachment configuration of the upper housing 110 and the lower housing 120 is also the same, a description thereof is omitted.

In the biosensor cartridge 100 of the second embodiment, the accommodating portion 119 can be formed differently from the first embodiment.

Referring to FIGS. 8 and 9, in the biosensor cartridge 100 according to the second embodiment, the accommodating portion 119 for accommodating the specimen in the upper housing 110 and guiding it to the sensor area of the lower sensor chip 500 is formed.

Specifically, the accommodating portion 119 is a space for inducing a reaction of a test target specimen with the exposed sensor area 540 by accommodating the test target specimen in a fluid state, e.g., in a liquid state, and the accommodating portion 119 is concavely recessed from the upper surface to form a conical passage, i.e., a channel, the diameter of which becomes narrower as it approaches the sensor area 540.

Accordingly, the accommodating portion 119 is formed to have an inclined surface 118 such that the diameter W1 of the opening of the upper surface is larger than the diameter of the opening W2 at the distal end of the accommodating portion 119.

In the accommodating portion 119, since the diameter W1 of the opening of the upper surface is expanded to be wider than the area of the sensor chip 500, the difference between the diameter W1 of the opening of the upper surface and the diameter W2 of the opening at the distal end of the accommodating portion 119 is significantly large.

For example, the diameter W1 of the opening of the upper surface can satisfy two to three times the diameter W2 of the opening at the distal end of the accommodating portion 119.

As the difference between the diameter W1 of the opening in the upper surface and the diameter W2 of the opening at the distal end of the accommodating portion 119 becomes larger, the accommodating volume of the accommodating portion 119 increases, so that a large amount of specimen can be accommodated.

At this time, the inclination angle of the inclined surface 118—the angle of the inclined surface with respect to the horizontal direction in which the sensor chip 500 is placed when viewed from the cross section in FIG. 9—can be uniform, but can have an inflection point.

That is, the inclination angle increases as it approaches the sensor area 540, it forms a verticality in the outermost area closest to the sensor area 540, so that it can be changed to a cylindrical passageway.

As described above, since the accommodating portion 119 has the inclined surface 118, a concave groove having a depth that is a height from the upper surface of the upper housing 110 to the channel area is formed. A specimen is collected in the groove to induce a reaction with the probe material in the sensor area 540.

As described above, the biosensor cartridge 100 accommodates the biosensor chip 500 inside the housing 110, 120, and is provided to accommodate the circuit board 150 for transmitting the detection information of the sensor chip 500 to the external diagnostic device 200.

Hereinafter, the biosensor chip 500 of the present embodiment will be described with reference to FIGS. 10 to 13.

Figure 10:
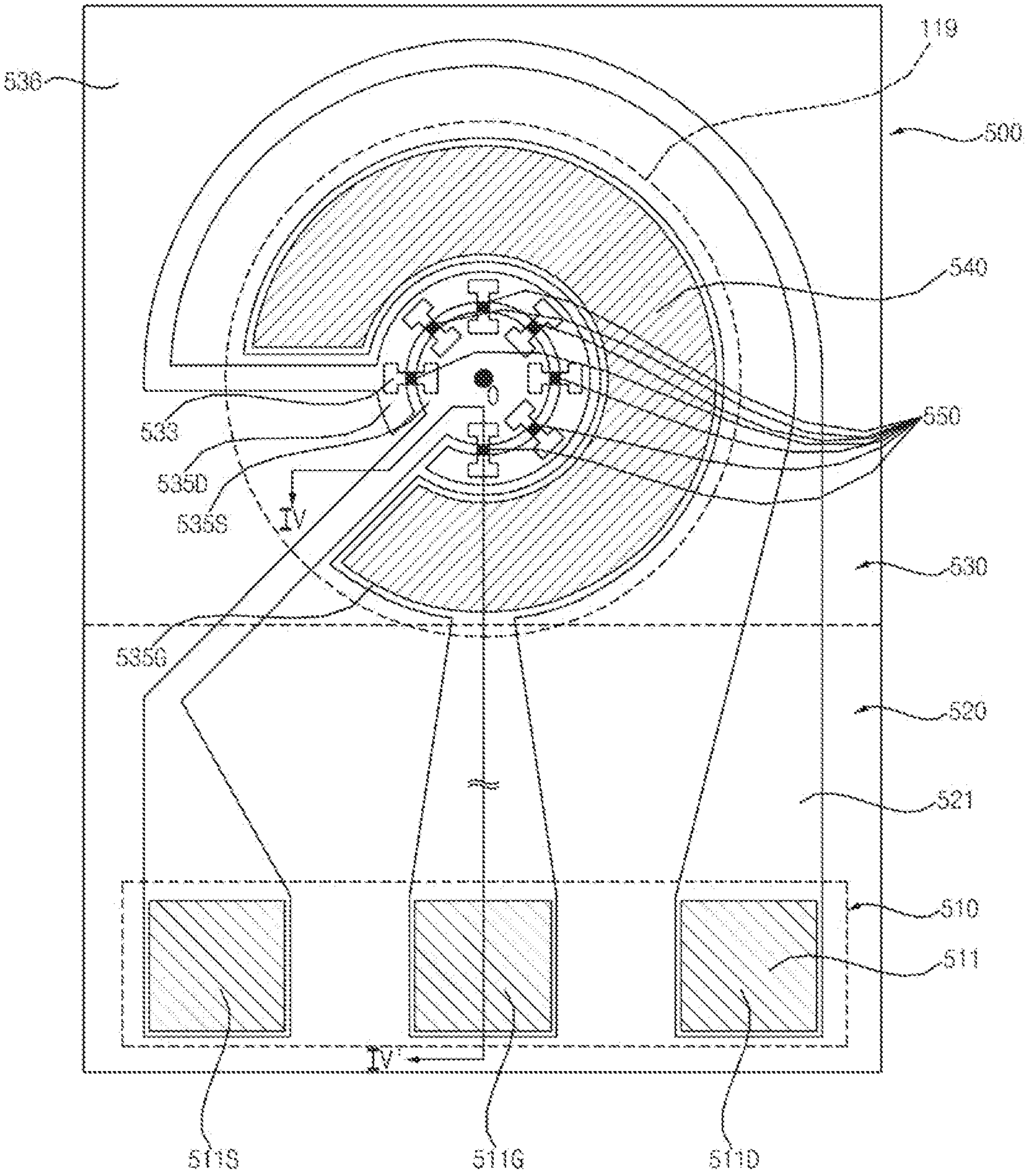
FIG. 10 is a top view of an example of a sensor chip applicable to the biosensor cartridge of FIGS. 6 to 8.
Figure 11:
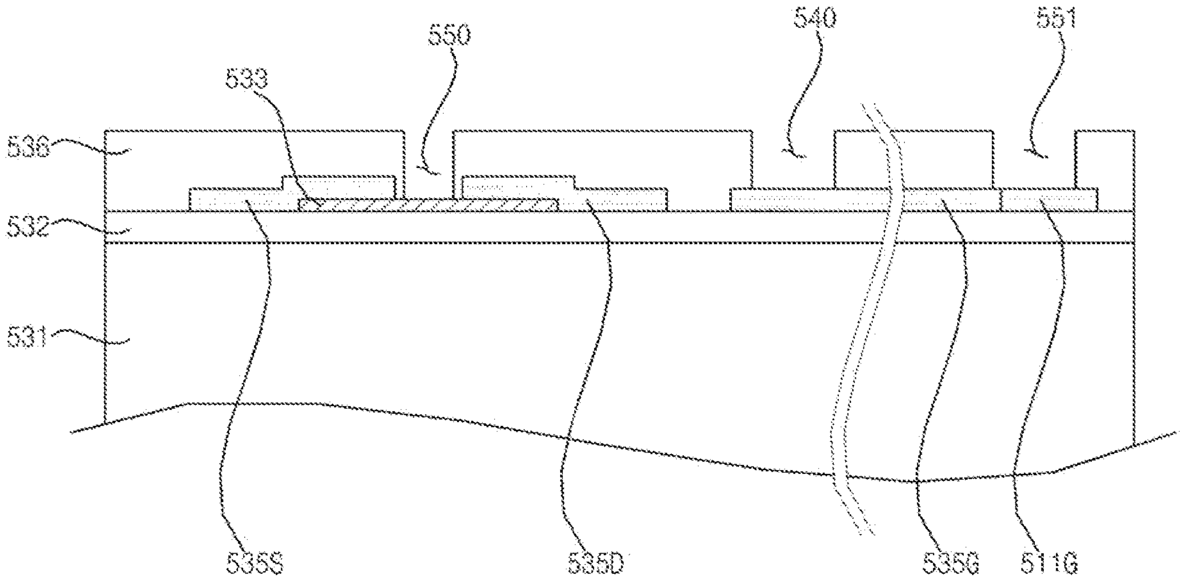
FIG. 11 illustrates the sensor chip of FIG. 10 taken along IV-IV'.
Figure 12A:
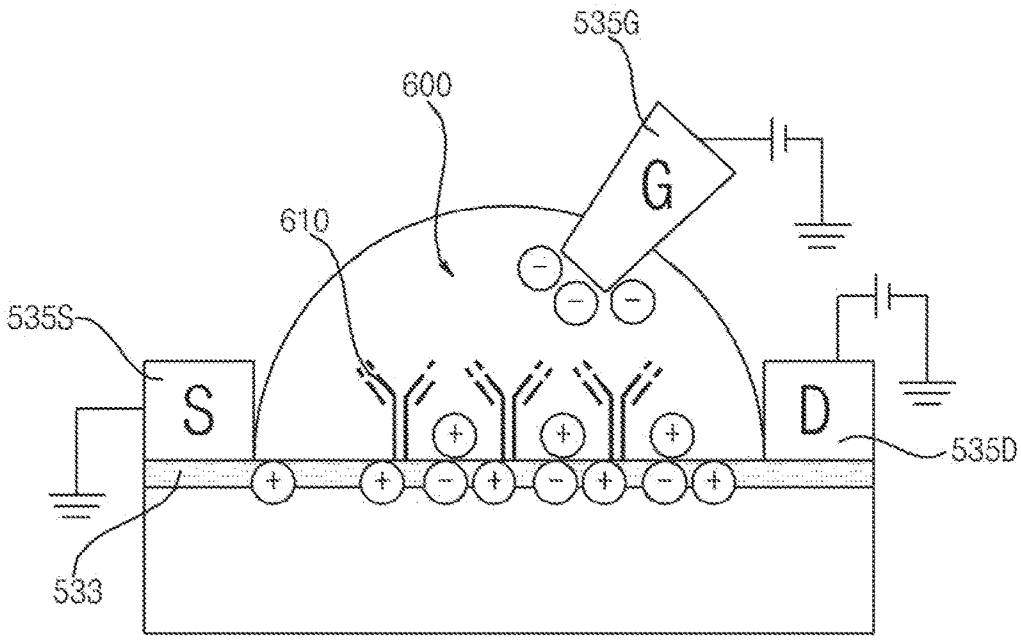
FIG. 12A and FIG. 12B are schematic diagram illustrating a reaction according to a target material of the sensor chip shown in FIG. 11.
Figure 12B:
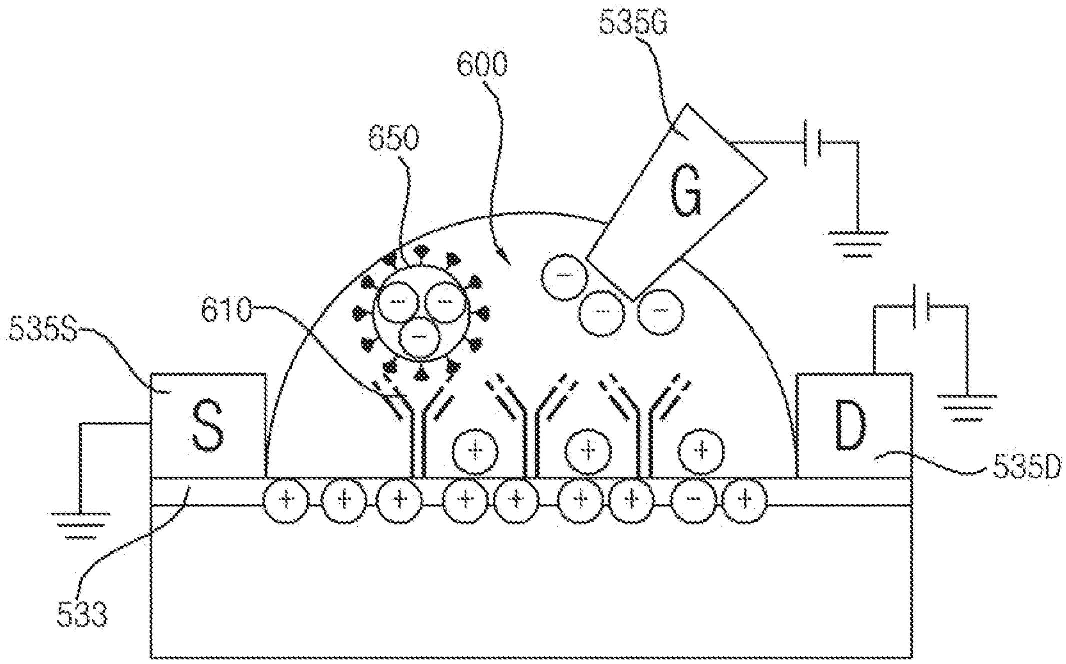
Figure 13:
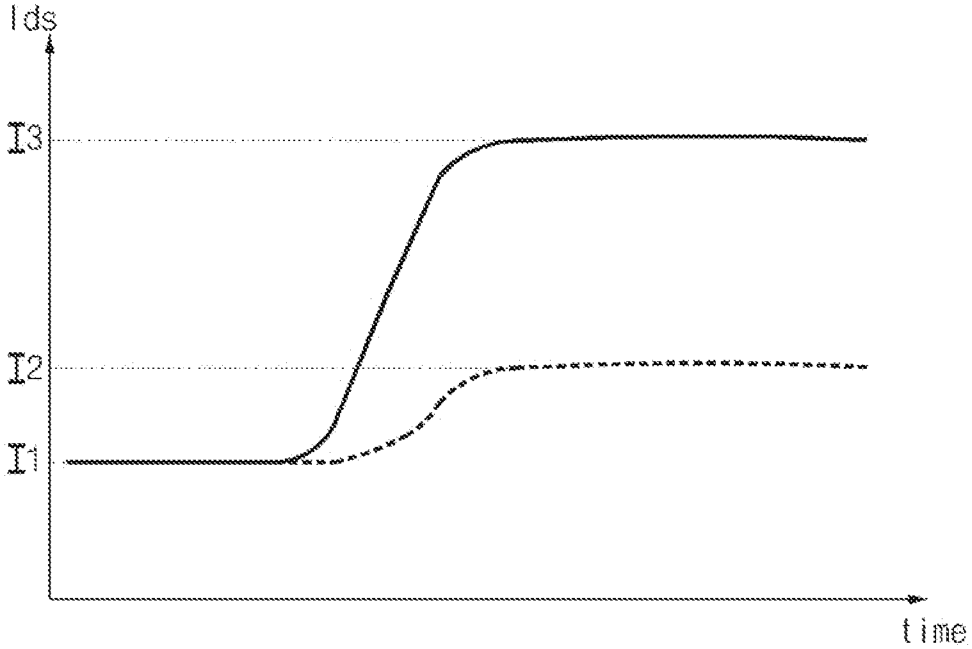
FIG. 13 is a graph illustrating changes of the output current of the sensor chip according to FIG. 12A and FIG. 12B.

FIG. 10 is a top view of an example of a sensor chip applicable to the biosensor cartridge of FIGS. 6 to 8, FIG. 11 illustrates the sensor chip of FIG. 10 taken along IV-IV', FIG. 12A and FIG. 12B are schematic diagram illustrating a reaction according to a target material of the sensor chip 500 shown in FIG. 11, and FIG. 13 is a graph illustrating changes of the output current of the sensor chip 500 according to FIG. 12A and FIG. 12B.

The biosensor chip 500 detects a target material from a specimen introduced into the inside by the accommodating portion 119 of the biosensor cartridge 100, and transmits an electrical signal generated by reacting with the detected target material to the pad 158 of the circuit board 150 through the electrode pad 511.

For example, the specimen can refer to saliva, a body fluid including sweat, blood, a solution diluted with serum or plasma, and the like, as a biological material.

The biosensor chip 500 is a semiconductor-based sensor chip 500, and can be manufactured as a biosensor chip 500 to which graphene is applied.

The sensor chip 500 can have various sizes depending on a size of the target material, the number of the target materials, and the size of the cartridge 100, and can be designed with a size of 6*6 mm or 6*8 mm, for example.

Referring to FIG. 10 and FIG. 11, the biosensor chip 500 according to the embodiment can have a plane of rectangular shape, a sensor area 540 exposed to exterior through the accommodating portion 119 in the front surface is formed, and can be divided into the pad area 510 connected to the pad 158 of the circuit substrate 150 through the connecting member 140, which is spaced from the sensor area 540, and a connection portion 530 that connects the sensor area 540 and the pad area 510.

The sensor area 540 detects a target material from the contacted specimen, and probe material that react with the target material to generate an electrical signal, e.g., an antigen, an antibody, an enzyme, and the like are attached thereto.

When the sensor area 540 comes into contact with a specimen, it interacts with a target material included in the specimen to generate an electrical signal. Accordingly, the external diagnostic device 200 connected to the biosensor 100 can analyze an electrical signal generated from the biosensor 100 to detect the presence or concentration of the target material.

The sensor area 540 includes a transistor structure, and has a structure where probe material is attached to a channel area 550 of the transistor.

Specifically, the sensor area 540 includes a plurality of circular or ring-shaped electrodes 535S, 535D, and 535G forming a concentric circle, and a plurality of channel areas 550 are between the plurality of electrodes 535S, 535D, and 535G, particularly, between the source electrode 535S and the drain electrode 535D.

An insulating layer 532 is formed on the semiconductor substrate 531, and the insulating layer 532 can be formed of oxide or nitride. When the semiconductor substrate 531 is a silicon substrate, the insulating layer 532 can be formed of silicon oxide or silicon nitride, and can be formed by various methods. For example, a silicon oxide layer can be formed on the surface through heat treatment or via chemical etching.

A plurality of channels 533 are formed on the insulating layer 532 to be spaced apart from each other.

A plurality of channels 533 are disposed spaced apart by a certain distance from the center O of the sensor area 540, and a central area of each channel 533 is exposed to form the channel area 550.

That is, the plurality of channels 533 are disposed to be spaced apart from each other on the circumference of an imaginary circle having a certain length as a radius in the center O of the circle.

The plurality of channels 533 can be disposed to be spaced apart by the same angle. For example, as shown in FIG. 10, seven channels 533 can be formed, and each channel 533 can be spaced apart at an angle of 45 degrees.

Alternatively, five channels 533 can be disposed so that each channel 533 can be spaced apart at an angle of 60 degrees. However, the channels 533 can be spaced apart by any angle.

One channel 533 can be patterned in a specific shape, and can be formed of a semiconductor material. Alternatively, one channel 533 can be formed of a graphene based material that is highly reactive as a highly conductive material.

The shape of one channel 533 includes areas overlapping with the source electrode 535S and the drain electrode 535D, and a channel area 550 exposed to the outside through the accommodating portion 119 in the two overlapping areas.

As shown in FIG. 10, the channel area 550 has the channel 533 formed with an I-shape to have a width smaller than the overlapping area to have smaller resistance in the channel area 550, but not limited thereto, and can be formed with a bar type to have the same width throughout the overlapping area to the channel 533.

The source electrode 535S having the shape of a circle having the smallest diameter can be formed on the center O of the sensor area 540, and is formed to overlap with an end part of the channel 533, and overlaps with the plurality of channels 533 to simultaneously transmit the source voltage to the plurality of channels 533.

Meanwhile, a drain electrode 535D can be formed on the outer periphery of the channel area 550 to be spaced apart from the source electrode 535S.

The drain electrode 535D can be formed in a ring shape, and is formed along the circumference of an imaginary circle that surrounds the channel area 550 and has a greater diameter than that of the channel area 550.

The drain electrode 535D also simultaneously overlaps with the drain overlapping area 552 of the plurality of channels 533 to simultaneously receive current from the plurality of channels 533.

An end portion of the drain electrode 535D is cut off and forms a passage through which the connection portion 521 of the source electrode 535D passes.

Meanwhile, a gate electrode 535G is formed along the circumference of an imaginary circle having a larger diameter surrounding the drain electrode 535D.

The gate electrode 535G has the largest area and can occupy ½ to ⅔ of the sensor area 540. The gate electrode 535G is formed to be spaced apart from the source electrode, the gate electrode 535S, 535D, and the channel area 550.

An end portion of the drain electrode 535D is also cut off and forms a passage through which the connection portion 521 of the drain electrode 535D and the source electrode 535S passes.

The electrodes 535S, 535D, and 535G of the sensor area 540 designed as shown in FIG. 10 are formed in the same layer.

Accordingly, the source electrode, the drain electrode, and the gate electrodes 535S, 535D, and 535G are all formed in the same layer and formed in one process.

For example, the source electrode, the drain electrode, and the gate electrode 535S, 535D, and 535G can be respectively formed by forming an electrode layer and simultaneously patterning a corresponding electrode layer.

Thus, a process step can be reduced, and a process time and cost can be reduced by simultaneously forming three electrodes 535S, 535D, and 535G that do not overlap each other.

The metal layer can be formed of at least one of Ni, Cu, Zn, Pd, Ag, Cd, Pt, Ga, In, and Au, but is not limited thereto.

A passivation layer 536 is formed on the electrodes 535S, 535D, and 535G.

The passivation layer 536 is formed on the entire sensor chip 500 to protect the sensor area 540 and the electrodes 535S, 535D, and 535G.

The passivation layer 536 can be formed of a material resistant to moisture, and can be formed of, for example, an oxide layer, a nitride layer, such as a silicon nitride, or a carbide layer.

In addition, the passivation layer 536 can be applied with a polymer resin, but is not limited thereto.

The passivation layer 536 exposes only the upper portion 551 of the plurality of channel areas 550, the gate electrode 535G, and the plurality of pads 511 in the sensor chip 500, and covers all other areas. Specifically, the source electrode 535S is electrically connected to a source pad 511S, the drain electrode 535D is electrically connected to the drain pad 511D and the gate electrode 535G is connected to the gate pad 511G, as illustrated in FIG. 8.

Accordingly, the area exposed by the passivation layer 536 is very limited.

In particular, in the sensor area 540, only the gate electrode 535G and the channel area 550 are exposed to induce a reaction by directly contacting the specimen.

In the pad area 510, each pad 511S, 511D, 511G is exposed in an insulated state, and electrically in contact with each pad 158 of the circuit board 150 through a connecting member (e.g., connecting member 140).

As shown in FIG. 12A, probe material 610 is attached to each of the channel areas 550 and is exposed as described above to activate the sensor.

The probe material 610 is a material that reacts specifically to a target material to be detected by the sensor. When the target material is an antigen, an antibody can be attached thereto, or when the target material is an antibody, an antigen can be attached thereto.

When the channel 533 is formed of graphene, a linker material (not shown) can be attached for smooth connection between the probe material 610 and graphene, and a process of attaching the probe material 610 after attaching a linker material on graphene is defined as an activation process.

The linker material is different depending on the material constituting the channel 533 and the probe material 610, and in the case of graphene, it can be a polymer structure having a nano size, for example, can be formed of at least one of polyurethane, polydimethylsiloxane, Norland Optical Adhesives NOA, epoxy, polyethylene terephthalate, polymethyl methacrylate, polyimide, polystyrene, polyethylene naphtharate, polycarbonate, and combinations thereof.

In addition, the linker material can be formed of a combination of polyurethane and NOA (e.g., NOA 68) or another UV-curable polymer. However, the linker material is not limited thereto, and can be made of various polymers having flexibility.

FIGS. 12A and 12B are schematic diagrams illustrating a reaction of the sensor chip 500.

When the target material does not exist in the specimen as shown in FIG. 12A, the source electrode 535S receives a source voltage and the gate electrode 535G receives a gate voltage by the voltage applied to each pad 511.

The gate electrode 535G is exposed to the accommodating portion 119 and comes into contact with the specimen provided from the outside to apply a bias voltage to the specimen. Therefore, the specimen exists in a state of being partially charged with respect to the voltage of the gate electrode 535G.

At this time, the drain current Ids (e.g., in ampere) read from the drain electrode 535D is as shown in FIG. 13.

That is, when there is no target material reacting with the probe material 610 in the specimen 600, the drain current Ids has a first value I1, which is defined as a reference current.

At this time, as shown in FIG. 12B, when the target material 650 exists in the specimen 600, the channel 533 is charged with a specific carrier as the target material 650 reacts with the probe material 610. For example, as shown in FIG. 12B, a depletion state in which charges are accumulated in the channel 533 can proceed.

Accordingly, as the drain current Ids read from the drain electrode 535D increases, it has a second value I2 of FIG. 13.

At this time, the amount of accumulated charge is proportional to the area of the channel 533. Thus, when the number of channels 533 is one, the drain current Ids has a second value I2. When the number of channels 533 is two or more, the drain current Ids has a third value I3 greater than the second value I2. When the number of channels 533 is three or more, the drain current Ids has a fourth value I4 greater than the third value I2, and so on. Accordingly, the value of the drain current Ids read from the drain electrode 535D is amplified with the number of channels 533.

At this time, even when one channel 533 does not operate as the plurality of channels 533 are spaced apart from each other, the existence of the target material can be recognized by causing the drain current Ids to increase or decrease in another channel 533.

As described above, the graphene channel sensor chip 500 has a multi-channel structure having a plurality of channels spaced apart from each other, thereby amplifying a drain current and compensating for a malfunctioning channel.

In such a sensor chip 500, both the gate electrode 535G and the channel area 550 can be exposed by the distal end opening of the accommodating portion 119 having a circle larger than the circumference of the gate electrode 535G.

In addition, the plurality of channel areas 550 are formed to be spaced apart at the same angle and at the same distance from the center O of the sensor area 540 opened by the accommodating portion 119 such that the specimen is uniformly contacted, and formed in a shape surrounding the source and drain electrodes 535S and 535D in order to dispose the channel 533 between the source and drain electrodes 535S and 535D, thereby optimizing a structure.

In FIG. 10, the connection portion 521 is respectively included, which is connected from an end of each of the electrodes 535S, 535D, and 535G to the pad 511, and each connection portion 521 is formed of the same metal layer as the electrodes 535S, 535D, and 535G, and not overlapped with each other.

FIG. 10 shows that the pads 511 are formed in serial (e.g., in series) at an end of the sensor chip 500, but not limited thereto.

The design of the sensor chip 500 can be variously changed so long as the transistor in which the gate electrode 535G and the plurality of channels 533 are exposed is maintained in the accommodating portion 119.

Accordingly, the position of the pad(s) 511 can also be variously changed. However, the positions of the connecting member 140 and the connection pad(s) 158 of the circuit board 150 are also changed according to the change in the position of the pad(s) 511.

As such, the biosensor cartridge 100 that accommodates the graphene based multi-channel sensor chip 500 and the biosensor diagnostic device 200 coupled therewith form a single biosensor system environment.

At this time, the biosensor diagnostic device 200 and the biosensor cartridge 100 perform the diagnosis and the sensor certification simultaneously by inserting the connection terminal 153 of the biosensor cartridge 100 to the insertion hole 2914 of the cartridge insertion module 2911 of the biosensor diagnostic device 200.

Hereinafter, a diagnosis method according to the embodiment is described with reference to FIG. 14 to FIG. 17.

Figure 14:
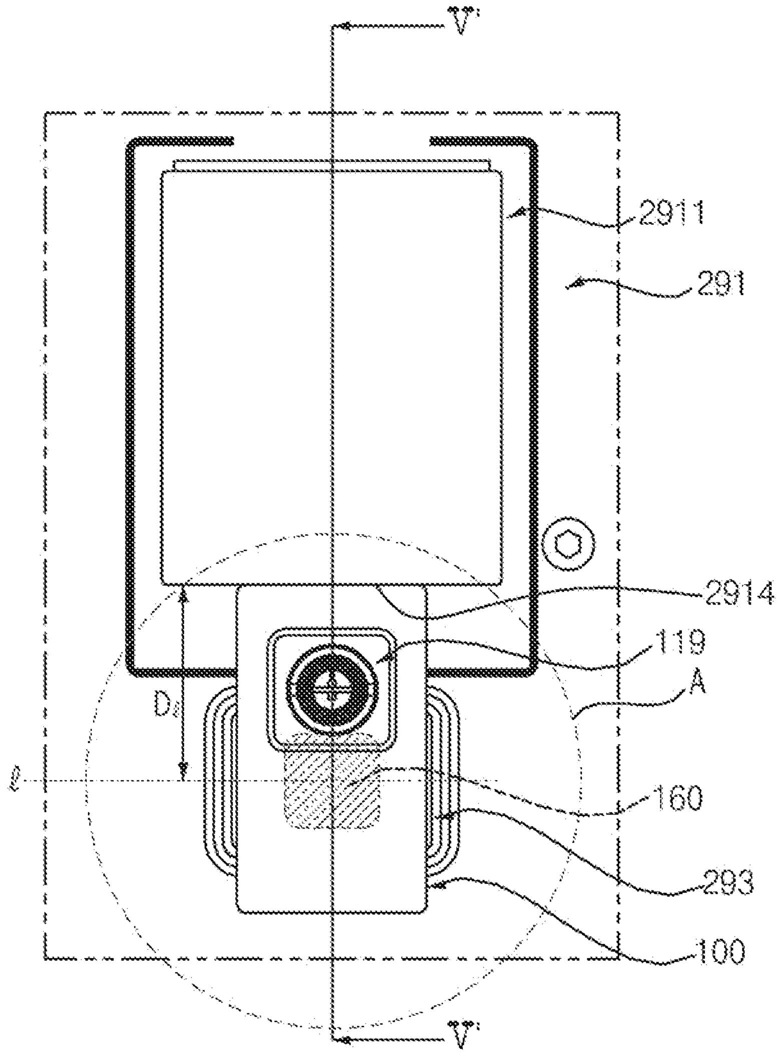
FIG. 14 is a coupling diagram in which the biosensor cartridge is coupled to the biosensor diagnostic device in the biosensor system of FIG. 1.
Figure 15:
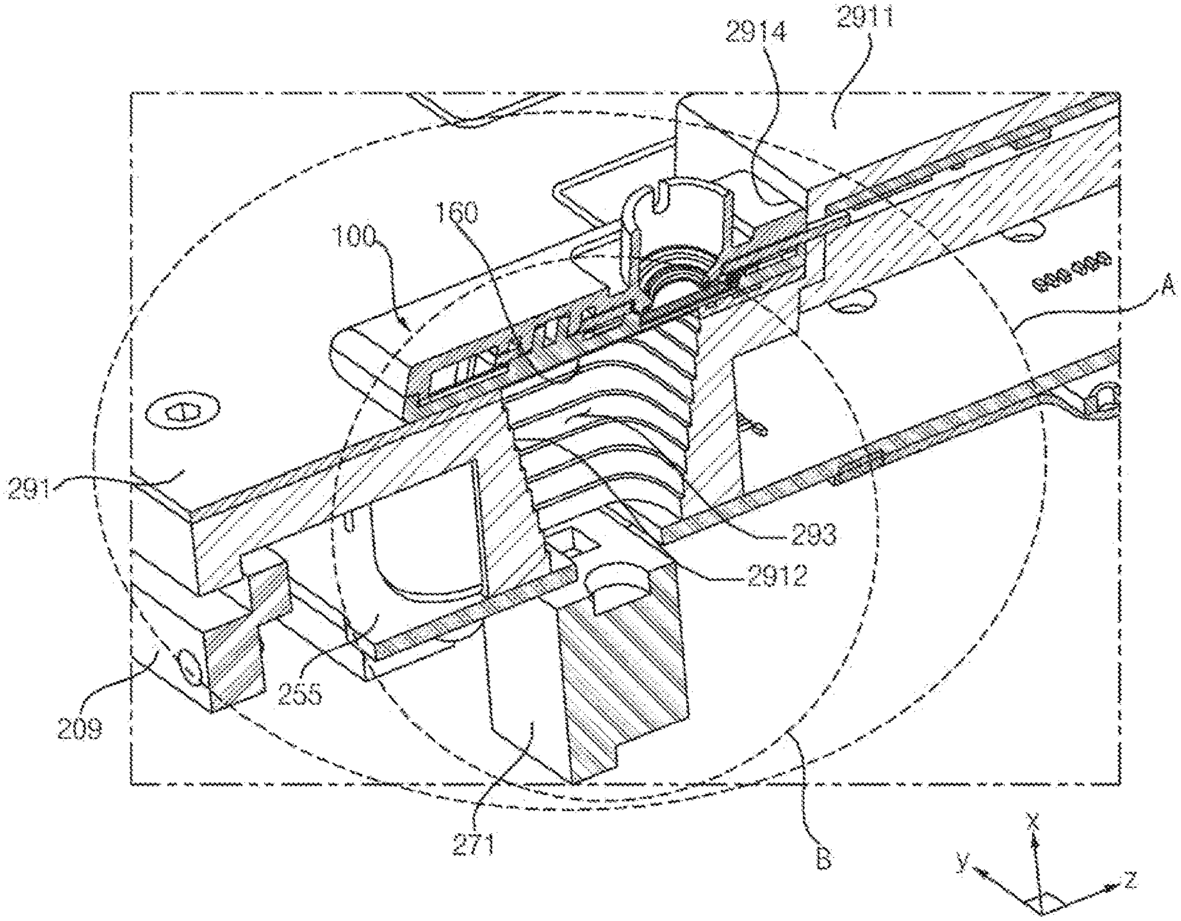
FIG. 15 is a cross-sectional perspective view taken along line V-V' in the coupling diagram of FIG. 14.
Figure 16:
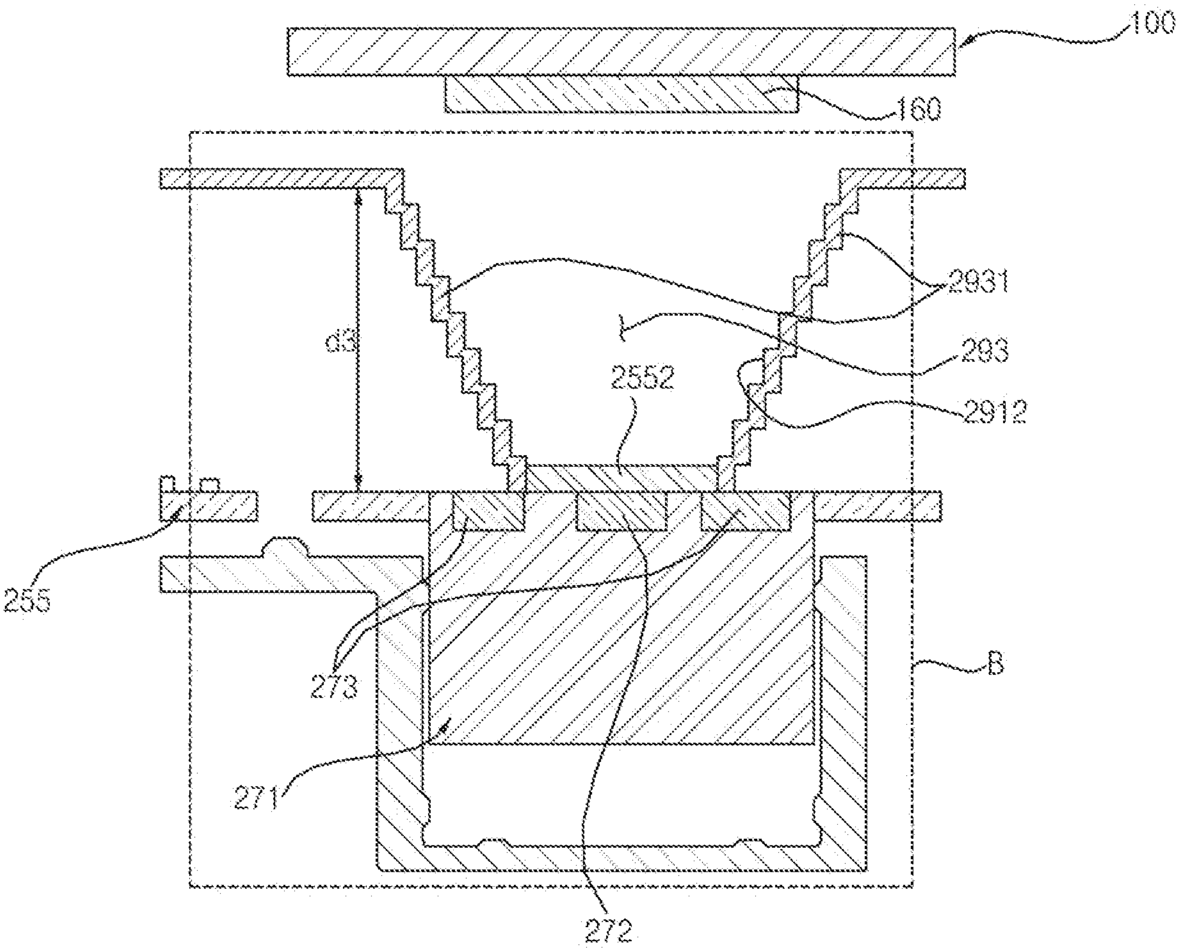
FIG. 16 is a cross-sectional front view facing the cross-section of FIG. 15.

FIG. 14 is a coupling diagram in which the biosensor cartridge 100 is coupled to the biosensor diagnostic device 200 in the biosensor system of FIG. 1, FIG. 15 is a cross-sectional perspective view taken along line V-V' in the coupling diagram of FIG. 14, and FIG. 16 is a cross-sectional front view facing the cross-section of FIG. 15.

As shown in FIGS. 14 to 16, when a test target specimen is received in the accommodating portion 119 of the biosensor cartridge 100 in the biosensor system according to the present embodiment, the connection terminal 153 of the biosensor cartridge 100 is inserted into the insertion hole 2914 of the cartridge insertion module 2911 of the biosensor diagnostic device 200.

As described above, the specimen can be a body fluid, such as saliva or sweat, or blood.

When a plurality of insertion holes 2914 are disposed, the connection terminal 153 is inserted into the insertion hole 2914 of a type matching the type of the connection terminal 153.

The insertion of the cartridge connection terminal 153 can be performed in the same manner as the insertion of the USB memory as the cartridge connection terminal 153 is similar to the USB terminal.

As described above, when the biosensor cartridge 100 and the biosensor diagnostic device 200 are coupled for analysis, the state shown in FIG. 14 to FIG. 16 is maintained.

That is, the accommodating portion 119 in which the test targeting specimen is accommodated is located outside the diagnostic device 200, and transmits an electrical signal in a state in which only the connection terminal 153 is inserted into the diagnostic device 200 through the insertion hole 2914.

Referring to FIG. 15, when the diagnostic device 200 and the cartridge 100 are coupled, the cartridge 100 can be spaced apart from the front panel 291, but alternatively, the cartridge 100 can contact the front panel 291.

At this time, the rear surface 129 of the lower housing 120 of the cartridge 100 faces the front panel 291, and the QR label 160 attached to the rear surface 129 of the lower housing 120 is aligned with the QR opening 293 of the front panel 291.

The QR opening 293 is aligned with the QR reading module 271 which is disposed at a lower side thereof through a light guide part, and the QR reading module 271 includes a QR camera module 272 and at least one light source module 273 in the case as shown in FIG. 16. Two light source modules 273 can be provided, with the QR camera module 272 being disposed between the two light source modules 273. However, more than two light source modules 273 can also be provided, with each light source module 273 facing the QR opening 293.

The QR reading module 271 is disposed at the lower side of the light guide part 2912, and the QR camera module 272 and the at least one light source module 273 are disposed toward the QR opening 293, which is an upper part of the light guide part 2912.

In this case, a QR reader device 272, which is the QR camera module, is disposed aligned with a center line of the QR opening 293, and at least one light source module 273 is disposed around (e.g., symmetrically around) the QR reader device 272.

When a plurality of the light source modules 273 are disposed, the plurality of the light source modules 273 can be disposed with being spaced apart with each other while maintaining the same distance with the QR reader device 272 at the center. In this case, an LED module can be applied to the light source modules 273, but not limited thereto.

The light guide part 2912 can have an inclined surface of which a diameter becomes narrower as being closer to the QR reading module 271, and the diameter of the second opening 293 at the upper surface of the front panel 291 has the greatest value. Therefore, as seen from the upper surface of the front panel 291, the light guide part 2912 of which the diameter converges to the QR reading module 271 is formed.

As shown in FIG. 16, a light guide plate 2931 can disposed on the surface of the light guide part 2912. Accordingly, as seen from the upper surface of the front panel 291, a tunnel structure is provided, which is surrounded by the light guide plate 2931 of which the diameter converges to the QR reading module 271.

As such, the light guide plate 2931 collects light of the light source module 273 emitted from the lower side and delivers the light to the upper side, when the QR reader device 272 reads a code of the QR label 160 of the cartridge 100, the light guide plate 2931 can provide light, which is deficient, and can function as a lighting part that provides uniform light by extending the light from the at least one light source module 273, which is a point light source, which can direct light towards the QR label 160.

In this case, a protection sheet 2552 can be attached to the upper surface of the QR reading module 271, and the protection sheet 2552 can prevent the lower side of the QR reader device 272 from being contaminated by foreign material or dust. That is, the protection sheet 2552 can be disposed directly on the QR reader device 272.

As described above, when the cartridge 100 to which the QR label 160 is attached is inserted into the diagnostic device 200, the diagnostic device 200 performs genuine product certification of the inserted biosensor cartridge 100 before performing diagnosis through the connection terminal 153.

Hereinafter, a method of diagnosing the diagnostic device 200 when the biosensor cartridge 100 is inserted and cartridge product certification are described in the biosensor system.

Figure 17:
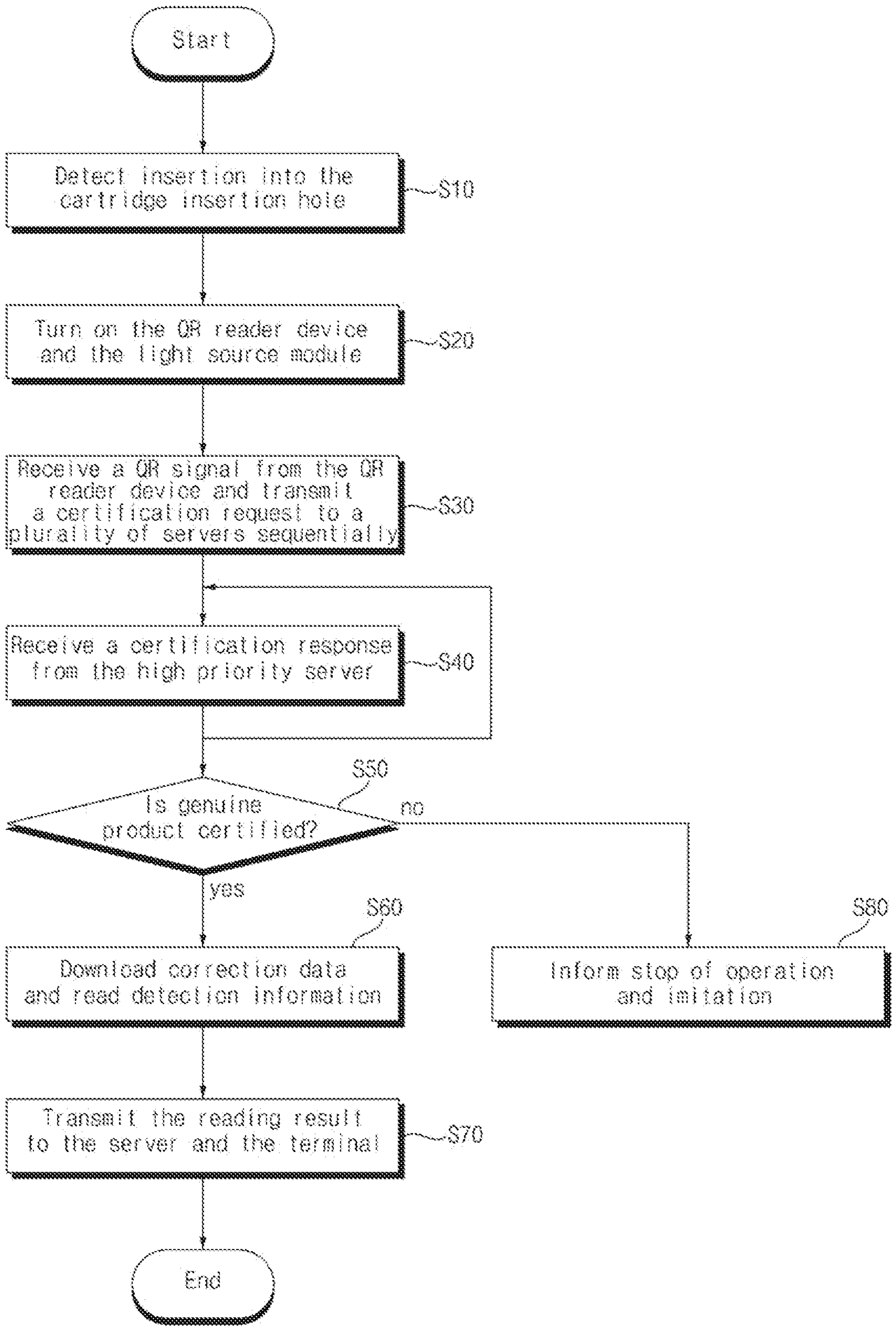
FIG. 17 is a flowchart illustrating an operation of the biosensor diagnostic device when the biosensor cartridge is inserted in the biosensor system.

FIG. 17 is a flowchart illustrating an operation of the biosensor diagnostic device 200 when the biosensor cartridge 100 is inserted in the biosensor system.

As described above, on the rear surface 129 of the lower housing 120 of the biosensor cartridge 100, i.e., the rear surface 129 of the cartridge 100 exposed to the outside, a QR label 160 including a QR code in which sensor information including a product ID and a manufacturing serial number for genuine product certification of the biosensor cartridge 100 is stored is attached.

When the biosensor cartridge 100 is inserted into the insertion module 2911 of the biosensor diagnostic device 200, the biosensor diagnostic device 200 detects that the connection terminal 153 of the biosensor cartridge 100 is inserted into the insertion hole 2914 and coupled, and transmits a cartridge detection signal to the operation unit 250 (step S10).

The operation unit 250 functions as a processor (e.g., hardware embedded processor) for controlling the entire modules of the biosensor diagnostic device 200, and when the cartridge detection signal is transmitted from the insertion module 2911, the operation unit 250 transmits an operation command to the QR reading module 271 (step S20).

While the QR reader device 272 and the light source module 273 of the QR reading module 271 are turned on and transmit light to the upper side of the front panel 291, the camera of the QR reader device 272 reads a QR code of the QR label 160 at the rear surface 129 of the cartridge 100 on the QR opening 293.

The QR information read from the QR reader device 272 is transmitted to the operation unit 250.

The operation unit 250 decodes the QR information to extract sensor information stored as QR information. In this case, the sensor information can include linker information, target material information, product ID, sensor chip ID, vendor information, manufacturer information, manufacturing date, assembly date, test date, and the like.

The operation unit 250 can transmit a certification request of the biosensor cartridge 100 to the at least one cloud server 400 connectable through the wireless communication module 261 (step S30).

The operation unit 250 transmits the certification request to the highest priority cloud server 400 of which priority is high among a plurality of connectable cloud servers 400 first, and waits a certification response for a predetermined time.

In this case, the priority can be configurable for each diagnostic device 200, and a vendor server can be configured as the highest priority. When the vendor server is disposed in a distributed manner into a plurality of regions, the priority is configurable depending on the distance to the diagnostic device 200 or response time. In this case, if the certification response is not received within a predetermined time from the highest priority cloud server 400 (step S40), the operation unit 250 can transmit the certification request again to the next highest priority cloud server 400.

As described above, the operation unit 250 transmits the certification request to the cloud servers 400 of the priority for a plurality of cloud servers 400, and if the certification response is not received within a predetermined time, the operation unit 250 transmits the certification request to the next highest priority cloud 400, and it can be prevented to progress the certification and the certification response simultaneously in a plurality of cloud servers 400.

When the certification response is received from one of the cloud servers 400, the operation unit 250 stops the certification request and receives the genuine product certification of the cartridge while transmitting and receiving signals with the cloud server 400 from which the response is received (step S50).

That is, the operation unit 250 transmits all types of the QR information to the cloud server 400 that transmits the certification response, and the cloud server 400 performs certification of the cartridge by comparing the QR information with information of the vendor server.

The operation unit 250 receives the certification result on whether the biosensor cartridge 100 currently inserted is a genuine product from the cloud server 400.

In the case that the biosensor cartridge 100 is a genuine product, the operation unit 250 downloads correction data from the cloud server 400 (step S60) and reads a detection signal of the connection terminal 153 from the sensor controller 240, the signal conversion amplifier 210, and the signal filtering unit 220 by driving the cartridge insertion module 2911.

At this time, the gate voltage and the source voltage are transmitted to the cartridge 100 through the sensor controller 260, and the drain current that is changed accordingly is read from the signal conversion amplifier 210.

Such read drain current value is amplified, and digitized after noise is removed by the signal filtering unit 220, and transmitted to the operation unit 250.

A detection signal is decoded by executing a stored algorithm with respect to the drain current value, which is the transmitted digitized detection signal, thereby reading whether the target material exists in the specimen currently accommodated in the cartridge 100.

At this time, the operation unit 250 downloads the correction data for a corresponding cartridge from the cloud server 400 after genuine product certification, and accordingly upgrades a corresponding algorithm, so that the optimized algorithm for the accumulated results of the same type of cartridge can be applied to the analysis.

The operation unit 250 reads the detection signal by performing the upgraded algorithm, and transmits the result to the display module 295 for visualization (S70).

In addition, it can operate to transmit a corresponding reading result to the cloud server 400, and transmit to a connected user terminal 300, so that a user can be notified by a designated user terminal 300 (S80).

Meanwhile, in the case that the cartridge 100 is not a genuine product, operation unit 250 stops the operation and informs that the currently inserted cartridge 100 is not a genuine product through the display module 295.

The biosensor is not easy to determine whether it is an imitation. Even if it is genuine, sensor errors are often found from test data accumulated after manufacturing and sales. Therefore, a process of classifying the biosensor cartridge 100 in which an error has occurred is required before the test proceeds.

The biosensor system of the present embodiment can check an error including a current risk to a corresponding type of the biosensor cartridge 100 through such a certification procedure.

In addition, as the insertion of cartridge 100 and the genuine product certification are performed simultaneously, certification is performed by using a separate QR reader, and then the certified cartridge is applied to the diagnostic device 200 so that two-step operation of diagnosis can be merged into one operation. Therefore, the user's convenience is increased, and the genuine product certification of cartridge and the cartridge diagnosis are performed almost simultaneously and proceeded in a state where the cartridge inserted, so that the diagnosis result of a corresponding cartridge and the information of the cartridge are not mixed and can be clearly matched.

The disclosure can provide a biosensor cartridge connected with a diagnostic devices through a terminal of the circuit substrate, which is connected to the sensor chip and minimize the influence exerted on the sensor chip when being connected with a diagnostic device.

In addition, according to the disclosure, a separate memory chip that stores environment information for genuine product certification of the biosensor on the circuit substrate is not mounted, and the cost is saved, and there is an effect of minimizing the volume of the cartridge.

Furthermore, a QR code for storing environment information is attached to an outer surface of the cartridge, and the cartridge can have a compact size, and the matching error between detection information and the environment information can be minimized by reading the QR code at the outer surface of the cartridge.

Furthermore, according to the disclosure, a QR reader device is aligned to read the QR code of the biosensor cartridge in the diagnostic device when a terminal of the biosensor cartridge is inserted, and a separate distance or position adjustment is not required, and accordingly, the diagnosing time can be saved, and the diagnosing process can be simplified.

Various embodiments described herein may be implemented in a computer-readable medium using, for example, software, hardware, or some combination thereof. For example, the embodiments described herein may be implemented within one or more of Application Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, micro-controllers, microprocessors, other electronic units designed to perform the functions described herein, or a selective combination thereof. In some cases, such embodiments are implemented by the controller. For Example, the controller is a hardware-embedded processor executing the appropriate algorithms (e.g., flowcharts) for performing the described functions and thus has sufficient structure. Also, the embodiments such as procedures and functions may be implemented together with separate software modules each of which performs at least one of functions and operations. The software codes can be implemented with a software application written in any suitable programming language. Also, the software codes can be stored in the memory and executed by the controller, thus making the controller a type of special purpose controller specifically configured to carry out the described functions and algorithms. Thus, the components shown in the drawings have sufficient structure to implement the appropriate algorithms for performing the described functions.

For a software implementation, the embodiments such as procedures and functions may be implemented together with separate software modules each of which performs at least one of functions and operations. The software codes can be implemented with a software application written in any suitable programming language. Also, the software codes may be stored in the memory and executed by the controller. Thus, the components shown in the drawings have sufficient structure to implement the appropriate algorithms for performing the described functions.

The present invention encompasses various modifications to each of the examples and embodiments discussed herein. According to the invention, one or more features described above in one embodiment or example can be equally applied to another embodiment or example described above. The features of one or more embodiments or examples described above can be combined into each of the embodiments or examples described above. Any full or partial combination of one or more embodiment or examples of the invention is also part of the invention.

What is claimed is:

1. A diagnostic device for a biosensor cartridge that generates an electronic detection signal depending on a target material in an applied analysis specimen, the diagnostic device comprising:

a main board having an internal space for mounting at least one functional module;

a cover member for accommodating the main board;

a front panel for covering an upper surface of the cover member and providing a display area, the front panel including an insertion hole for receiving the biosensor cartridge and an opening located to be aligned with a QR code located on a lower surface of the biosensor cartridge when the biosensor cartridge is in contact with the front panel and connected to the diagnostic device through the insertion hole;

a control module configured to analyze the detection signal from the biosensor cartridge and display a presence of the target material in the display area; and a QR reading module arranged to correspond to the opening of the front panel and configured to read the QR code of the biosensor cartridge.

2. The diagnostic device of claim 1, wherein the control module is configured to communicate with a server through a network to perform genuine product certification involving certifying whether the biosensor cartridge inserted into the insertion hole is genuine.

3. The diagnostic device of claim 2, wherein the control module is configured to:

obtain sensor information from the QR code read by from the QR reading module; and perform the genuine product certification with the server based on the sensor information.

4. The diagnostic device of claim 3, wherein the server is among a plurality of servers, and wherein the control module is configured to:

transmit a certification request to a highest priority server among the plurality of servers; and based on a certification response corresponding to the certification request not being received within a predetermined time, transmit the certification request to the next highest priority server.

5. The diagnostic device of claim 2, wherein the control module is configured to, in response to the biosensor cartridge being certified as genuine, read the detection signal from the biosensor cartridge and determine whether the target material is present.

6. The diagnostic device of claim 2, wherein, when the certification is completed, the control module is configured to receive read correction data for the biosensor cartridge from the server and update a read algorithm by the read correction data.

7. The diagnostic device of claim 1, wherein the QR reading module includes:

a QR reader device configured to photograph the QR code; and a light source module disposed around the QR reader device for irradiating light to the opening of the front panel.

8. The diagnostic device of claim 7, wherein the front panel includes:

a light guide part through which light is delivered from the light source module to the opening, the light guide part including an inclined surface having a width that becomes narrower from the opening of the front panel; and a light guide plate disposed on the inclined surface of the light guide part and converting the light from the light source module to a planar light source and delivering the light to the opening of the front panel.

9. The diagnostic device of claim 1, wherein the control module is configured to:

match sensor information obtained from the QR code through the QR reading module with a reading result of the biosensor cartridge; and store data in which the sensor information and the reading result are matched.

10. The diagnostic device of claim 1, further comprising a battery providing power to the at least one functional module, wherein the biosensor diagnostic device is provided as a portable integrated device.

* * * * *